US007604952B2

(12) United States Patent
Holvoet et al.

(10) Patent No.: US 7,604,952 B2
(45) Date of Patent: Oct. 20, 2009

(54) DETECTION AND DETERMINATION OF THE STAGES OF CORONARY ARTERY DISEASE

(75) Inventors: Paul N. Holvoet, Kessel-Lo (BE); Désiré J. Collen, London (GB)

(73) Assignee: Leuven Research & Development VZW, Leuven (BG)

( * ) Notice: Subject to any disclaimer, the term of this patent is extended or adjusted under 35 U.S.C. 154(b) by 90 days.

(21) Appl. No.: 11/654,097

(22) Filed: Jan. 16, 2007

(65) Prior Publication Data

US 2007/0190586 A1    Aug. 16, 2007

Related U.S. Application Data

(60) Division of application No. 10/174,797, filed on Jun. 18, 2002, now Pat. No. 7,166,469, which is a continuation of application No. 09/906,560, filed on Jul. 16, 2001, now abandoned, which is a continuation of application No. 09/148,158, filed on Sep. 4, 1998, now Pat. No. 6,309,888.

(51) Int. Cl.
G01N 33/92 (2006.01)

(52) U.S. Cl. ............ 435/7.1; 435/7.92; 435/7.93; 435/7.94; 435/7.95; 435/967; 435/973; 436/540; 436/546; 436/548; 436/13; 436/15; 436/71; 436/517; 436/819

(58) Field of Classification Search ............ 435/7.1, 435/7.2, 7.21, 7.92–7.95, 967, 973; 436/540, 436/546, 548, 13, 15, 171, 517, 809; 530/380, 530/388.1, 388.15, 388.25
See application file for complete search history.

(56) References Cited

U.S. PATENT DOCUMENTS

| 4,444,879 | A | | 4/1984 | Foster et al. |
|---|---|---|---|---|
| 5,024,829 | A | | 6/1991 | Berger et al. |
| 5,026,537 | A | | 6/1991 | Daddona et al. |
| 5,046,499 | A | | 9/1991 | Berger |
| 5,120,834 | A | | 6/1992 | Gargan et al. |
| 5,196,324 | A | | 3/1993 | Bumol et al. |
| 5,223,410 | A | | 6/1993 | Gargan et al. |
| 5,362,649 | A | | 11/1994 | Schwertner |
| 5,380,667 | A | | 1/1995 | Schwertner |
| 5,396,886 | A | | 3/1995 | Cuypers |
| 5,453,359 | A | | 9/1995 | Gargan et al. |
| 5,487,892 | A | | 1/1996 | Gargan |
| 5,597,726 | A | | 1/1997 | Bumol et al. |
| 5,604,105 | A | * | 2/1997 | Jackowski ............ 435/7.4 |
| 5,658,729 | A | | 8/1997 | Hayden |
| 5,690,103 | A | | 11/1997 | Groth et al. |
| 5,710,008 | A | | 1/1998 | Jackowski |
| 5,756,067 | A | | 5/1998 | Redgrave et al. |

| 6,040,147 | A | | 3/2000 | Ridker et al. |
|---|---|---|---|---|
| 6,309,888 | B1 | * | 10/2001 | Holvoet et al. ............ 436/71 |
| 6,727,102 | B1 | * | 4/2004 | Holvoet et al. ............ 436/501 |
| 7,166,469 | B2 | * | 1/2007 | Holvoet et al. ............ 435/7.1 |
| 7,229,775 | B2 | * | 6/2007 | Holvoet et al. ............ 435/7.1 |
| 7,390,627 | B2 | * | 6/2008 | Holvoet et al. ............ 435/7.1 |
| 2003/0100486 | A1 | | 5/2003 | Ridker et al. |
| 2003/0152566 | A1 | | 8/2003 | Schonbeck et al. |

FOREIGN PATENT DOCUMENTS

| EP | 0 484 863 A1 | 5/1992 |
|---|---|---|
| EP | 0 433 088 B1 | 6/1997 |
| JP | 4-173096 | 6/1992 |

(Continued)

OTHER PUBLICATIONS

Holvoet et al., OxidizedLow Density Lipoproteins In Patients With Transplant-Associated Coronary Artery Disease, Arterioscler. Thromb. Vasc. Biol. 18(1): 100-107 (Jan. 1998).*

(Continued)

*Primary Examiner*—Gailene R Gabel
(74) *Attorney, Agent, or Firm*—Bryan Cave LLP; Stephen P. Gilbert, Esq.

(57) ABSTRACT

A method having clinically sufficient degree of diagnostic accuracy for detecting the presence of coronary artery disease in a human patient from the general population and for distinguishing between the stages of the disease in that patient is disclosed. The stages are, first, the non-acute stage, which is either asymptomatic coronary artery disease or stable angina, second, the acute stage known as unstable angina, and, third, the acute stage known as acute myocardial infarction. The diseased state (as opposed to the non-diseased state) is indicated by the clinically significant presence of a first marker in a sample from the patient. The presence of one of the two acute stages, unstable angina or acute myocardial infarction, is indicated by the clinically significant presence of a second marker in a sample from the patient. The presence of the more severe acute stage known as acute myocardial infarction is indicated by the clinically significant presence of a third marker in a sample from the patient. Preferably the first marker comprises OxLDL, the second marker comprises MDA-modified LDL, and the third marker is a troponin. Preferably the OxLDL and MDA-modified LDL are detected using monoclonal antibodies that can detect the presence of those markers in undiluted human plasma at concentrations as low as 0.02 milligrams/deciliter.

17 Claims, No Drawings

FOREIGN PATENT DOCUMENTS

| JP | KOKAI 8-304395 | 11/1996 |
|---|---|---|
| JP | KOKAI 9-5323 | 10/1997 |
| WO | WO 94/23302 | 10/1994 |
| WO | PCT/EP97/03287 | 6/1997 |
| WO | PCT/EP97/03493 | 7/1997 |
| WO | WO 98/59248 | 12/1998 |

OTHER PUBLICATIONS

Holvoet et al., Malondialdehyde-Modified Low Density Lipoproteins In Patients With Atherosclerotic Disease, J. Clin. Invest. 95: 2611-2619 (1995).*

Holvoet et al., "Association Between Circulating Oxidized Low-Density Lipoprotein And Incidence Of The Metabolic Syndrome," JAMA, vol. 299, No. 19, pp. 2287-2293 (May 21, 2008)(available at JAMA website on May 20, 2008).

Adams JE, 3d, Bodor GS, Davila-Roman VG, Delmez JA, Apple FS, Ladenson JH, Jaffe AS. "Cardiac Troponin I. A Marker With High Specificity For Cardiac Injury," *Circulation*. 1993; 88(1): 101-106.

American Biogenetic Sciences Inc. *1995 Annual Report*. 24 pages (1995).

*American Biogenetic Sciences. Focus on Diagnostic Tests: A Technology Anaylsis. Updated Full Report*. 33 pages. Paisley and Habermas, Inc. (Jun. 3, 1996).

American Biogenetic Sciences, Inc., "Renal dialysis joint venture announced by American Biogenetic Sciences, Inc. and Gull Laboratories, Inc." News Release (Sep. 26, 1996).

American Biogenetic Sciences, Inc. Jesup & Lamont Securities Corporation, "New Buy Recommendation dated Mar. 28, 1996" (12 pages.).

Antman EM, Tanasijevic MJ, Thompson B, Schactman M, McCabe CH, Cannon CP, Fischer GA, Fung AY, Thompson C, Wybenga D, Braunwald E. "Cardiac-Specific Troponin I Levels To Predict The Risk Of Mortality In Patients With Acute Coronary Syndromes." *N. Eng. J. Med*. 1996; 335(18): 1342-1349.

AtheroGenics, Inc. Printout of Web Site (www.atherogenics.com). Home page and "Technology Platform" and "In The News" sections. 17 pages (printed Jun. 8, 1998).

Aviram M, Maor I. "Phospholipase D-Modified Low Density Lipoprotein Is Taken Up By Macrophages At Increased Rate. A Possible Role For Phosphatidic Acid." *J. Clin. Invest*. 1993; 91: 1942-1952.

Berliner JA, Heinecke JW. "The Role Of Oxidized Lipoproteins In Atherogenesis," *Free Radical Biology & Medicine* 1996; 20(5): 707-727.

Brown MS, Goldstein JL. "Lipoprotein Metabolism In the Macrophage: Implications For Cholesterol Deposition In Atherosclerosis." *Annu. Review Biochem*. 1983; 52: 223-261.

Cartier R, Dagenais F, Hollmann C, Cambron H, Buluran J. "Chronic Exposure To Cyclosporin Affects Endothelial And Smooth Muscle Reactivity In The Rat Aorta." *Ann. Thorac. Surg*. 1994; 58: 789-794.

Chen CH, Nguyen HH, Weilbaecher D, Luo S, Gotto Jr. AM, Henry PD. "Basic Fibroblast Growth Factor Reverses Atherosclerotic Impairment Of Human Coronary Angiogenesis-Like Responses In Vitro." *Atherosclerosis* 1995; 116: 261-268.

Chin JH, Azhar S, Hoffman BB. "Inactivation Of Endothelial Derived Relaxing Factor By Oxidized Lipoproteins." *J. Clin. Invest*. 1992; 89: 10-18.

Cockcroft DW, Gault MH. "Prediction of creatinine clearance from serum creatinine." *Nephron* 1976; 16: 31-41.

Crisp SJ, Dunn JM, Rose ML, Barbir M, Yacoub MH. "Antiendothelial Antibodies After Heart Transplantation: The Accelerating Factor In Transplant-Associated Coronary Artery Disease?" *J. Heart Lung Transplant*. 1994; 13(1, Part 1): 81-92.

Declerck PJ, Mombaerts P, Holvoet P, De Mol M, Collen D. "Fibrinolytic Response And Fibrin Fragment D-Dimer Levels In Patients With Deep Vein Thrombosis." *Thromb. Haemost*. 1987; 58(4): 1024-1029.

Degoulet P, Legrain M, Reach I, Aime F, Devries C, Rojas P, Jacobs C. "Mortality Risk Factors In Patients Treated By Chronic Hemodialysis." *Nephron* 1982; 31: 103-110.

Esterbauer H, Jurgens G, Quehenberger Q, Koller E. "Autooxidation Of Human Low Density Lipoprotein: Loss Of Polyunsaturated Fatty Acids And Vitamin E And Generation Of Aldehydes." *J. Lipid Res.*. 1987; 28: 495-509.

Farber HW, Barnett HF. "Differences In Prostaglandin Metabolism In Cultured Aortic And Pulmonary Arterial Endothelial Cells Exposed To Acute And Chronic Hypoxia." *Circ. Res*. 1991; 68(5): 1446-1457.

Fogelman MA, Shechter, I, Seager J, Hokom M, Child JS, Edwards PA. "Malondialdehyde Alteration Of Low Density Lipoproteins Leads To Cholesteryl Ester Accumulation In Human Monocyte-Macrophages." *Proc. Natl. Acad. Sci. USA* 1980; 77(4): 2214-2218.

Folcik VA, Nivar-Aristy RA, Krajewski LP, Cathcart MK. "Lipoxygenase Contributes To The Oxidation Of Lipids In Human Atherosclerotic Plaques." *J. Clin. Invest*. 1995; 96: 504-510.

Friedman JA, Dwyer JT. "Hyperhomocysteinemia As A Risk Factor For Cardiovascular Disease In Patients Undergoing Hemodialysis." *Nutr. Rev*. 1995; 53(7): 197-201.

Galle J, Bengen J, Schollmeyer P, Wanner C. "Oxidized Lipoprotein(A) Inhibits Endothelium-Dependent Dilation: Prevention By High Density Lipoprotein." *Eur. J. Pharmacol*. 1994; 265: 111-115.

Galle J, Schollmeyer P, Wanner C. "Cyclosporin And Oxidized Low Density Lipoproteins Synergistically Potentiate Vasoconstriction: Influence Of The Endothelium." *Eur. Heart J*. 1993; 14(Suppl. I): 111-117.

Gerrity RG. "The Role Of The Monocyte In Atherogenesis. I. Transition Of Blood-Borne Monocytes Into Foam Cells In Fatty Lesions." *Am. J. Pathol*. 1981; 103(2): 181-190.

Grattan MT, Moreno-Cabral CE, Starnes VA, Oyer PE, Stinson EB, Shumway NE. "Cytomegalovirus Infection Is Associated With Cardiac Allograft Rejecting And Atherosclerosis." *J. Am. Med. Assoc*. 1989; 261(24): 3561-3566.

Haberland MD, Fogelman AM, Edwards PA. "Specificity Of Receptor-Mediated Recognition Of Malondialdehyde-Modified Low Density Lipoproteins." *Proc. Natl. Acad. Sci USA*. 1982; 79: 1712-1716.

Haberland ME, Olch CL, Fogelman AM. "Role Of Lysines In Mediating Interaction Of Modified Low Density Lipoproteins With The Scavenger Receptor Of Human Monocyte Macrophages." *J. Biol. Chem*. 1984; 259(18): 11305-11311.

Hamm WC, Goldmann BU, Heeschen C, Kreymann G, Berger J, Meinertz T. "Emergency Room Triage Of Patients With Acute Chest Pain By Means Of Rapid Testing For Cardiac Troponin T Or Troponin I." *N. Eng. J. Med*. 1997; 337(23): 1648-1653.

Hamm WC, Goldmann BU, Heeschen C, Kreymann G, Berger J, Meinertz T. "Emergency Room Triage Of Patients With Acute Chest Pain By Means Of Rapid Testing For Cardiac Troponin T Or Troponin I." *N. Eng. J. Med*. 1997; 337(23): 1648-1653. Letters concerning same and authors' reply, published in *N. Eng. J. Med*. 1998; 338(18): 1314-1315.

Hammer A, Kager G, Dohr G, Rabl H, Ghassempur I, Jurgens G. "Generation, Characterization, And Histochemical Application Of Monoclonal Antibodies Selectively Recognizing Oxidatively Modified ApoB-Containing Serum Lipoproteins." *Arterioscler. Thromb. Vasc. Biol*. 1995; 15(5): 704-713.

Hansson GK, Libby P. (eds.). *Immune Functions of the Vessel Wall*, vol. II (Harwood Academic Publishers 1996). Chapter 9: Witztum JL, Palinski W. "Autoimmunity To Oxidized Lipoproteins." pp. 159-171.

Havel RJ, Eder HA, Bragdon JH. "The Distribution And Chemical Composition Of Ultracentrifugally Separated Lipoproteins In Human Serum." *J. Clin. Invest*. 1955; 34: 1345-1353.

Heery JM, Kozak M, Stafforini DM, Jones DA, Zimmernam GA, McIntyre TM, Prescott SM. "Oxidatively Modified LDL Contains Phospholipids With Platelet-Activating Factor-Like Activity And Stimulates the Growth Of Smooth Muscle Cells." *J. Clin. Invest*. 1995; 96: 2322-2330.

Hlatky MA. "Evaluation Of Chest Pain In The Emergency Department." *N. Eng. J. Med*. 1997; 337(23): 1687-1689.

Hoff HF, O'Neill J. "Lesion-Derived Low Density Lipoprotein And Oxidized Low Density Lipoprotein Share A Lability For Aggregation, Leading To Enhanced Macrophage Degradation." *Arterioscler. Thromb*. 1991; 11(5): 1209-1222.

Hoff HF, O'Neill J, Chisolm III GM, Cole TB, Quehenberger O, Esterbauer H, Jurgens G. "Modification Of Low Density Lipoprotein With 4-Hydroxynonenal Induces Uptake By Macrophages." *Arteriosclerosis* 1989; 9(4): 538-549.

Hoffmeister HM, Jur M, Wendel HP, Heller W, Seipel L. "Alterations Of Coagulation And Fibrinolytic And Kallikrein-Kinin Systems In The Acute And Post-Acute Phases In Patients With Unstable Angina Pectoris." *Circulation* 1995; 91(10): 2520-2527.

Holvoet P, Perez G, Bernar H, Brouwers E, Vanloo B, Rosseneu M, Collen D. "Stimulation With A Monoclonal Antibody (mAb4E4) Of Scavenger Receptor-Mediated Uptake Of Chemically Modified Low Density Lipoproteins By THP-1-Derived Macrophages Enhances Foam Cell Generation." *J. Clin. Invest.* 1994; 93: 89-98.

Holvoet P, Collen D. "β-VLDL Hypercholesterolemia Relative To LDL Hypercholesterolemia Is Associated With Higher Levels Of Oxidized Lipoproteins And A More Rapid Progression Of Coronary Atherosclerosis In Rabbits." *Arterioscler. Thromb. Vasc. Biol.* 1997; 17(11): 2376-2382.

Holvoet P, Collen D. "Oxidized Lipoproteins In Atherosclerosis And Thrombosis." *FASEB J.* 1994; 8: 1279-1284.

Holvoet P, Collen D. "Thrombosis And Atherosclerosis." *Curr. Opinion Lipidol.* 1997; 8: 320-328.

Holvoet P, Perez G, Zhao Z, Brouwers E, Bernar H, Collen D. "Malondialdehyde-Modified Low Density Lipoproteins In Patients With Atherosclerotic Disease." *J. Clin. Invest.* 1995; 95: 2611-2619.

Holvoet P, Donck J, Landeloos M, Brouwers E, Luijtens K, Arnout J, Lesaffre E, Vanrenterghem Y, Collen D. "Correlation Between Oxidized Low Density Lipoproteins And Von Willebrand Factor In Chronic Renal Failure." *Thromb. Haemost.* 1996; 76(5): 663-669.

Holvoet P, Van Kleemput J, Collen D, Vanhaecke J. "Correlation Between Oxidized Low Density Lipoproteins And Coronary Artery Disease In heart Transplant Patients" Abstract published in *Final Programme* of 66th Congress of the European Atherosclerosis Society, Florence (Italy), Jul. 13-14, 1996; *Abstract Book*, p. 47.

Holvoet P, Stassen JM, Van Cleemput J, Collen D, Vanhaecke J. "Oxidized Low Density Lipoproteins In Patients With Transplant-Associated Coronary Artery Disease." *Arterloscler. Throm. Vasc. Biol.* 1998; 18(1): 100-107.

Holvoet P, Theilmeier G, Shivalkar B, Flameng W, Collen D. "LDL Hypercholesterolemia Is Associated With Accumulation Of Oxidized LDL, Atherosclerotic Plaque Growth, And Compensatory Vessel Enlargement In Coronary Arteries Of Miniature Pigs." *Arterioscler. Thromb. Vasc. Biol.* 1998; 18: 415-422.

Holvoet P, Collen D, Vanhaecke J. Presentation at 70th Scientific Session Of The American Heart Association, Orlando, Florida, Nov. 9-12, and published in abstract form in *Circulation* 1997; 96(Suppl. I): I417 (Abstract 2328).

Hruban RH, Beschorner WE, Baumbgartner WA, Augustine SM, Ren H, Reitz BA, Hutchins GM. "Accelerated Arteriosclerosis In Heart Transplant Recipients Is Associated Wtih A T-Lymphocyte-Mediated Endothelialitis." *Am. J. Pathol.* 1990; 137(4): 871-882.

Itabe H, Takeshima E, Iwasaki H, Kimura J, Yoshida Y, Imanaka T, Takano T. "A Monoclonal Antibody Against Oxidized Lipoprotein Recognizes Foam Cells In Atherosclerotic Lesions: Complex Formation Of Oxidized Phosphatidylcholines And Polypeptides." *J. Biol. Chem.* 1994; 269(21): 15274-15279.

Itabe H, Yamamoto H, Imanaka T, Shimamura K, Uchiyama H, Imura J, Sanaka T, Hata Y, Takano T. "Sensitive Detection Of Oxidatively Modified Low Density Lipoprotein Using A Monoclonal Antibody." *J. Lipid Res.* 1996; 37: 45-53.

Juckett MB, Balla J, Balla G, Jessurun J, Jacob HS, Vercellotti GM. "Ferritin Protects Endothelial Cells From Oxidized Low Density Lipoprotein In Vitro." *Am. J. Pathol.* 1995; 147(3): 782-789.

Kaplan R, Aynedjian HS, Schlondorff D, Bank N. "Renal Vasoconstriction Caused By Short-Term Cholesterol Feeding Is Corrected By Thromboxane Antagonist Or Probucol." *J. Clin. Invest.* 1990; 86: 1707-1714.

Keane WF, Mulcahy WS, Kassike BL, Kim Y, O'Donnell MP. "Hyperlipidemia And Progressive Renal Disease." *Kidney Int.* 1991; 39(Suppl.): S41-S48.

Kolata, G. "A New Generation Of Tests To Determine Heart Trouble." *New York Times News Service*. 7 pages (Nov. 26, 1995).

Koskinen P, Lemstrom K, Bruggeman C, Lautenschlager I, Hayry P. "Acute Cytomegalovirus Infection Induces A Subendothelial Inflammation (Endothelialitis) In The Allograft Vascular Wall. A Possible Linkage With Enhanced Allograft Arteriosclerosis." *Am. J. Pathol.* 1994; 144(1): 41-50.

Kotani K, Maekawa M, Kanno T, Kondo A, Toda N, Manabe M. "Distribution Of Immunoreactive Malondialdehyde-Modified Low-Density Lipoprotein In Human Serum." *Biochimica et Biophysica Acta* 1994; 1215: 121-125.

Libby P, Salomon RN, Payne DD, Schoen FJ, Pober JS. "Functions Of Vascular Wall Cells Related To Development Of Transplantation-Associated Coronary Arteriosclerosis" *Transplant. Proc.* 1989; 21(4): 3677-3684.

Lynch SM, Morrow JD, Roberts II LJ, Frei B. "Formation Of Non-Cyclooxygenase-Derived Prostanoids ($F_2$-Isoprostanes) In Plasma And Low Density Lipoproteins Exposed To Oxidative Stress In Vitro." *J. Clin. Invest.* 1994; 93: 998-1004.

Mabile L, Fitoussi G, Periquet B, Schmitt A, Salvayre R, Negre-Salvayre A. "Alpha-Tocopherol And Trolox Block The Early Intracellular Events (TBARS And Calcium Rises) Elicited By Oxidized Low Density Lipoproteins In Cultured Endothelial Cells." *Free Radic. Biol. Med.* 1995; 19(2): 177-187.

Menschikowski M, Kasper M, Lattke P, Schiering A, Schiefer S, Stockinger H, Jaross W. "Secretory Group II Phospholipase A2 In Human Atherosclerotic Plaques." *Atherosclerosis* 1995; 118: 173-181.

McCully KS. "Chemical Pathology Of Homocysteine. I. Atherogenesis." *Ann. Clin. Lab. Sci.* 1993; 23(6): 477-493.

Morrow JD, Awad JA, Boss HJ, Blair IA, Robert II LJ. "Non-Cyclogenase-Derived Prostanoids ($F_2$-isoprostanes) Are Formed In Situ On Phospholipids." *Proc. Natl. Acad. Sci. USA* 1992; 89: 10721-10725.

Muldoon MF et al., Ryan J et al., Oltrona L et al., and Liuzzo G et al. Letters and reply by authors. "C-Reactive Protein And Serum Amyloid A Protein In Unstable Angina." *N. Engl. J. Med.* 1995; 332(6): 398-400.

Murugesan G, Chisolm GM, Fox PL. "Oxidized Low Density Lipoprotein Inhibits The Migration Of Aortic Endothelial Cells In Vitro." *J. Cell. Biol.* 1993; 120(4): 1011-1019.

Neff MS, Eiser AR, Slifkin RF, Baum M, Baez A, Gupta S, Amarga E. "Patient Surviving 10 Years Of Hemodialysis." *Am. J. Med.* 1983; 74: 996-1004.

Ohman EM, Armstrong PW, Christenson RH, Granger CB, Katus HA, Hamm CW, O'Hanesian MA, Wagner GS, Kleiman NS, Harrell Jr. FE, Califf RM, Topol EJ. "Cardiac Troponin T Levels For Risk Stratification In Acute Myocardial Ischemia." *N. Eng. J. Med.* 1996 335(18): 1333-1341.

O'Marcaigh AS, Jacobson RM. "Estimating The Predictive Value Of A Diagnostic Test. How To Prevent Misleading Or Confusing Results." *Clin. Ped.* 1993; 32(8): 485-491.

Palinski W, Yla-Herttuala S, Rosenfeld ME, Butler SW, Socher SA, Parthasarathy S, Curtiss LK, Witztum JL. "Antisera And Monoclonal Antibodies Specific For Epitopes Generated During Oxidative Modification Of Low Density Lipoprotein." *Arteriosclerosis* 1990; 10(3): 325-335.

Parthasarathy S, Wieland E, Steinberg D. "A Role For Endothelial Cell Lipoxygenase In The Oxidative Modification Of Low Density Lipoprotein." *Proc. Nat. Acad. Sci. USA* 1989; 86: 1046-1050.

Penn MS, Chisolm GM, "Oxidized lipoproteins, altered cell function and atherosclerosis." *Atherosclerosis* 1994; 108(Suppl.): S21-S29.

Pocock SJ. *Clinical Trials. A Practical Approach*. Chapter 14: "Further Aspects Of Data Analysis." pp. 211-233. John Wiley & Sons. 1993.

Rasmussen O, Thomsen C, Ingerslev J, Hermansen K. "Decrease Of Von Willebrand Factor Levels After A High-Monounsaturated Fat Diet In Non-Insulin-Dependent Diabetic Subjects." *Metabolism* 1994; 43(11): 1406-1409.

Ravalli S, Marboe CC, D'Agati VD, Michler RE, Sigal E, Cannon PJ. "Immunohistochemical Demonstration Of 15-Lipoxygenase In Transplant Coronary Artery Disease." *Arterioscler. Thromb. Vasc. Biol.* 1995; 15(3): 340-348.

Reade V, Tailleux A, Reade R, Harduin P, Cachera C, Tacquet A, Fruchart JC, Fievet C. "Expression Of Apolipoprotein B Epitopes In Low Density Lipoproteins Of Hemodialyzed Patients." *Kidney Int.* 1993; 44: 1360-1365.

Reverter JC, Escolar G, Sanz C, Cases A, Villamor N, Nieuwenhuis HK, Lopez J, Ordinas A. "Platelet Activation During Hemodialysis Measured Through Exposure Of P-Selectin: Analysis By Flow Cytometric And Ultrastructural Techniques." *J. Lab. Clin. Med.* 1994; 124(1): 79-85.

Rose EA, Smith CR, Petrossian GA, Barr ML, Reemtsma K. "Humoral immune responses after cardiac transplantation: correlation with fatal rejection and graft atherosclerosis." *Surgery* 1989; 106(2): 203-208.

Rosenfeld ME, Palinski W, Yla-Herttuala, Butler S, Witztum JL. "Distribution Of Oxidation Specific Lipid-Protein Adducts And Apolipoprotein B In Atherosclerotic Lesions Of Varying Severity From Whhl Rabbits." *Arteriosclerosis* 1990; 10(3): 336-349.

Ross R. "The Pathogenesis Of Atherosclerosis: A Perspective For The 1990s." *Nature* 1993; 362: 801-809.

Salonen JT, Yia-Herttuala S, Yamamoto R, Butler S, Korpela H, Salonen R, Nyyssonen K, Palinski W, Witztum JL. "Autoantibody Against Oxidised LDL And Progression Of Carotid Atherosclerosis." *Lancet* 1992; 339(8798): 883-887.

Sasavage N. "Predicting Coronary Artery Disease. New Markers Could Identify Patients At Risk." *Clin. Lab. News* Mar. 1998; pp. 6-7.

Savenkova ML, Mueller DM, Heinecke JW. "Tyrosyl Radical Generated By Myeloperoxidase Is A Physiological Catalyst For The Initiation Of Lipid Peroxidation In Low Density Lipoprotein." *J. Biol. Chem.* 1994; 269(32): 20394-20400.

Schaffner T, Taylor K, Bartucci EJ, Fischer-Dzoga K, Beeson JH, Glagov S, Wissler RW. "Arterial Foam Cells With Distinctive Immunomorphologic And Histochemical Features of Macrophages." *Am. J. Pathol.* 1980; 100(1): 57-80.

Schulz T, Schiffl H, Scheithe R, Hrboticky N, Lorenz R. "Preserved Antioxidative Defense Of Lipoproteins In Renal Failure And During Hemodialysis." *Am. J. Kidney Dis.* 1995; 25(4): 564-571.

Selwyn AP, Kinlay S, Libby P, Ganz P. "Atherogenic Lipids, Vascular Dysfunctions, And Clinical Signs Of Ischemic Heart Disease." *Circulation* 1997; 95(1): 5-7.

Shultz EK. "Clinical Interpretation Of Laboratory Procedures." Chapter 14 in *Teitz, Fundamentals of Clinical Chemistry*. Burtis CA, Ashwood ER (eds.). 4th edition 1996. W.B.Saunders Company. pp. 192-199.

Sparrow CP, Olszewski J. "Cellular Oxidative Modification Of Low Density Lipoprotein Does Not Require Lipoxygenases." *Proc. Nat. Acad. Sci. USA* 1992; 89: 128-131.

Sparrow CP, Partharasathy S, Leake DS, Steinberg D. "Enzymatic Modification Of Low Density Lipoprotein By Purified Lipoxygenase Plus Phospholipase-$A_2$ Mimic Cell-Mediated Oxidative Modification." *J. Lipid Res.* 1988; 29: 745-753.

Steinberg D, Witztum JL. "Lipoproteins And Atherogenesis: Current Concepts." *J. Am. Med. Assoc.* 1990; 264(23): 3047-3052.

Steinberg D. "Clinical Trials Of Antioxidants In Atherosclerosis: Are We Doing The Right Thing?" *Lancet* 1995; 346: 36-38.

Steinberg D. "Lewis A. Conner Memorial Lecture. Oxidative Modification Of LDL And Atherogenesis." *Circulation* 1997; 95: 1062-1071.

Steinbrecher UP, Parthasarathy S, Leake DS, Witztum JL, Steinberg D. "Modification Of Low Density Lipoprotein By Endothelial Cells Involves Lipid Peroxidation And Degradation Of Low Density Lipoprotein Phospholipids." *Proc. Nat. Acad. Sci. USA* 1984; 81: 3883-3887.

Steinbrecher UP. "Oxidation Of Low Density Lipoprotein Results In Derivatization Of Lysine Residues Of Apolipoprotein B By Lipid Peroxide Decomposition Products." *J. Biol. Chem.* 1987; 262(8): 3603-3608.

Steinbrecher UP. Lougheed M. "Scavenger Receptor-Independent Stimulation Of Cholesterol Esterification In Macrophages By Low Density Lipoprotein Extracted From Human Aortic Intima." *Arterioscler. Thromb.* 1992; 12(5): 608-625.

Sutherland WH, Walker RJ, Ball MJ, Stapley SA, Robertson MC. "Oxidation Of Low Density Lipoproteins From Patients With Renal Failure Or Renal Transplants." *Kidney Int.* 1995; 48: 227-236.

Tamai O, Matsuoka H, Itabe H, Wada Y, Kohno K, Imaizumi T. "Single LDL Apheresis Improves Endothelium-Dependent Vasodilation In Hypercholesterolemic Humans." *Circulation* 1997; 95(1): 76-82.

Tanaka H, Sukhova GK, Swanson SJ, Cybulsky MI, Schoen FJ, Libby P. "Endothelial And Smooth Muscle Cells Express Leukocyte Adhesion Molecules Heterogeneously During Acute Rejection Of Rabbit Cardiac Allografts." *Am. J. Pathol.* 1994; 144(5): 938-951.

Trachtman H, Schwob N, Maesaka J, Valderrama E. "Dietary Vitamin E Supplementation Ameliorates Renal Injury In Chronic Puromycin Aminonucleoside Nephropathy." *J. Am. Soc. Nephrol.* 1995; 5(10): 1811-1819.

Tuzcu EM, Hobbs RE, Rincon G, Bott-Silverman C, De Franco AC, Robinson K, McCarthy PM, Stewart RW, Guyer S, Nissen SE. "Occult And Frequent Transmission Of Atherosclerotic Coronary Disease With Cardiac Transplantation. Insights From Intravascular Ultrasound." *Circulation* 1995; 91(6): 1706-1713.

Uchida K, Kanematsu M, Sakai K, Matsuda T, Hattori N, Mizuno Y, Suzuki D, Miyata T, Noguchi N, Niki E, Osawa T. "Protein-Bound Acrolein: Potential Markers For Oxidative Stress." *Proc. Natl. Acad. Sci. USA* 1998; 95: 4882-4887.

Van de Werf F. "Cardiac Troponins In Acute Coronary Syndromes." *N. Eng. J. Med.* 1996; 335(18): 1388-1389.

Zhao B, Dierichs R, Harrach-Ruprecht B, Winterhorff H. "Oxidized LDL Induces Serotonin Release From Blood Platelets." *Am. J. Hematol.* 1995; 48: 285-287.

Zwaginga JJ, Koomans HA, Sixma JJ, Rabelink TJ. "Thrombus formation And Platelet-Vessel Wall Interaction In The Nephrotic Syndrome Under Flow Conditions." J. Clin. Invest. 1994; 93: 204-211.

Zweig MH, Brosle SK, Reinhart RA. "ROC Curve Analysis: An Example Showing The Relationships Among Serum Lipid And Apolipoprotein Concentrations In Identifying Patients With Coronary Artery Disease." *Clin. Chem.* 1992; 38(8): 1425-1428.

Zaidi S, Pandey RN, Kidwai AM, Murti CRK. "A Rapid Method For Preparation Of Sarcolemma From Frog Leg Skeletal Muscle." *Chemical Abstracts* Jun. 7, 1982; 96(23) :19609le.

Palinski W, Rosenfeld ME, Ylä-Herttuala S, Gurtner GC, Socher SS, Butler SW, Parthasarathy S, Carew TE, Steinberg D, Witztum JL. "Low Density Lipoprotein Undergoes Oxidative Modification In Vivo." *Proc. Natl. Acad. Sci. USA* 1989; 86: 1372-1376.

Boyd H, Gown AM, Wolfbauer G, Chait A. "Direct Evidence For A Protein Recognized By A Monoclonal Antibody Against Oxidatively Modified LDL In Atherosclerotic Lesions From A Watanabe Hyperlipidemic Rabbit." *Am. J. Patho.* Nov. 1989; 135(5): 815-825.

Holvoet P, Vanhaecke J, Janssens S, Van de Werf F, Collen D. "Oxidized LDL And Malondialdehyde-Modified LDL In Patients With Acute Coronary Syndromes And Stable Coronary Artery Disease." *Circulation* 1998; 98: 1487-1494.

Ylä-Herttuala S, Palinski W, Rosenfeld ME, Parthasarathy S, Carew TE, Butler S, Witztum JL, Steinberg D. "Evidence For The Presence Of Oxidatively Modified Low Density Lipoprotein In Atherosclerotic Lesions Of Rabbit And Man." *J. Clin. Invest.* Oct. 1989; 84: 1086-1095.

Zawadzki Z, Milne RW, Marcel YL. "An Immunochemical Marker Of Low Density Lipoprotein Oxidation." *J. Lipid Res.* 1989; 30: 885-891.

Holvoet P, Collen D, Van de Werf F. "Malondialdehyde-Modified LDL As A Marker Of Acute Coronary Syndromes." *J. Am. Med. Assoc.* 1999; 281 (18): 1718-1721.

Copending U.S. Appl. No. 09/446,259, filed Dec. 20, 1999, entitled "Assays, Antibodies, And Standards For Detection Of Oxidized And MDA-Modified Low Density Lipoproteins" and naming Paul Holvoet and Désiré Collen as inventors, which application is the national stage of PCT/EP97/03493, filed Jul. 1, 1997 (which claims priority to PCT/EP97/03287, filed Jun. 20, 1997).

International Search Report, mailed by the International Searching Authority on Feb. 14, 2000, for International Patent Application No. PCT/IB99/01596, which PCT application corresponds to and claims priority from the above-captioned application.

Holvoet P. "Oxidative Modification Of Low-Density Lipoproteins In Atherothrombosis." *Acta Cardiol.* 1998; 53(5): 253-260.

WO 00/14548, published on Mar. 16, 2000, which is the international publication of application PCT/IB99/01596.

Written Opinion from International Examiner in PCT/EP97/03493.

Written Opinion from International Examiner in PCT/IB99/01596.

Holvoet P, Kritchevsky SB, Tracy RP, Mertens A, Rubin SM, Butler J, Goodpaster B, Harris TB. "The Metabolic Syndrome, Circulating Oxidized LDL, And Risk of Myocardial Infarction In Well-Functioning Elderly People In The Health, Aging, And Body Composition Cohort." *Diabetes*. 2004; 53(4): 1068-1073.

Sigurdardottir V, Fagerberg B, Hulthe J. "Circulating Oxidized Low-Density Lipoprotein (LDL) Is Associated With Risk Factors of The Metabolic Syndrome And LDL Size in Clinically Healthy 58-Year-Old Men (AIR Study)." *J Intern Med*. 2002; 252(5): 440-447.

Brody, JE. "Hunt For Heart Disease Tracks A New Suspect." *The New York Times*. 3 pages (Jan. 6, 2004).

Chapelle JP. "How Should We proceed When A Myocardial Infarction is Suspected," *Acta Clinica Belgica* 1984; 39(6): 393-395.

Hirschfield GM, Pepys MB. "C-reactive protein and cardiovascular disease: new insights from an old molecule." *Q J Med*. Nov. 2003; 96(11): 793-807.

Holvoet P, Mertens A, Verhamme P, Bogaerts K, Beyens G, Verhaeghe R, Collen D, Muls E, Van de Werf. "Circulating oxidized LDL is a useful marker for identifying patients with coronary artery disease." *Arterioscler Thromb Vasc Biol*. May 2001; 21(5): 844-848.

Holvoet P, Harris TB, Tracy RP, Verhamme P, Newman AB, Rubin SM, Simonsick EM, Colbert LH, Kritchevsky SB. "Association of high coronary heart disease risk status with circulating oxidized LDL in the well-functioning elderly: findings from the Health, Aging, and Body Composition study." *Arterioscler Thromb Vasc Biol*. Aug. 2003; 23(8): 1444-1448.

Hulthe J, Fagerberg B. "Circulating oxidized LDL is associated with subclinical atherosclerosis development and inflammatory cytokines (AIR Study)." *Arterioscler Thromb Vasc Biol*. Jul. 1, 2002; 22(7):1162-1167.

Lee TH, Goldman L. Serum Enzymes In The Diagnosis Of Acute Myocardial Infarction, *Annals of Internal Medicine* 1986; 105: 221-223.

Major AS, Dove DE, Ishiguro H, Su YR, Brown AM, Liu L, Carter KJ, Linton MF, Fazio S. "Increased Cholesterol Efflux In Apolipoprotein Al (ApoAl)-Producing Macrophages As A Mechanism For Reduced Atherosclerosis In ApoAl((-1-)) mice." *Arterioscler Thromb Vasc Biol*. Nov. 2001; 21(11): 1790-1795.

Ridker PM, Glynn, RJ, Hennekens, CH. "C-Reactive Protein Adds To The Predictive Value Of Total And HDL Cholesterol In Determining Risk Of First Myocardial Infaction." *Circulation* 1998; 97:2007-2011.

Ridker PM, Buring JE, Shih J, Matias M, Hennekens CH. "Prospective Study Of C-Reactive Protein And The Risk Of Future Cardiovascular Events In Stable And Unstable Angina." *Circulation* 1998; 98:731-733.

Schonbeck U, Gerdes N, Varo N, Reynolds RS, Horton DB, Bacendiek U, Robbie L, Ganz P, Kinlay S, Libby P. "Oxidized Low-Density Lipoprotein Augments And 3-Hydroxy-3-Methylglutanyl Coenzyme A Reductase Inhibitors Limit CD40 And CD40l Expression In Human Vascular Cells." *Circulation* 2002; 106(23): 2888-2893.

Shacter E. "Quantification And Significance Of Protein Oxidation In Biological Samples." *Drug Metab Rev*. Aug.-Nov. 2000;32(3-4): 307-26.

Varo N, de Lemos JA. Libby P, Morrow DA, Murphy SA, Nuzzo R, Gibson CM, Cannon CP, Braunwald E, Schonbeck U. "Soluble CD40L: Risk Prediction After Acute Coronary Syndromes." *Circulation* 2003; 108(9): 1049-1052.

Wentworth P Jr, Nieva J, Takeuchi C, Galve R, Wentworth AD, Dilley RB, DeLaria GA, Saven A, Babior BM, Janda KD, Eschenmoser A, Lerner RA. "Evidence for ozone formation in human atherosclerotic arteries." *Science* 2003; 302(5647): 1053-1056.

Holvoet P. "Oxidized LDL And Coronary Heart Disease," *Acta Cardiol*. Oct. 2004; 59(5): 479-484.

Cesari M, Kritchevsky SB, Nicklas BJ, Penninx BW, Holvoet P, Koh-Banerjee P, Cummings SR, Harris TB, Newman AB, Pahor M. "Lipoprotein peroxidation and mobility limitation: results from the health, aging, and body composition study." *Arch Intern Med*. Oct. 10, 2005; 165(18): 2148-2154.

Meisinger C, Baumert J, Khuseyinova N, Loewel H, Koenig W. "Plasma oxidized low-density lipoprotein, a strong predictor for acute coronary heart disease events in apparently healthy, middle-aged men from the general population," *Circulation*. Aug. 2, 2005; 112(5): 651-657 (Epub Jul. 25, 2005).

Mercodia AB. "Triple-Marker Test"; 4-page brochure (photocopied onto 2 sheets); Nov. 2004.

Johnston N, Jernberg T, Lagerqvist B, Siegbahn A, Wallentin L. "Improved Identification Of Patents With Coronary Artery Disease By The Use Of New Lipid And Lipoprotein Biomarkers," *Am J Cardiol*. Mar. 1, 2006; 97(5): 640-645; Epub Jan. 10, 2006.

Johnston N, Jernberg T, Lagerqvist B, Siegbahn A, Wallentin L. "Oxidized Low-Density Lipoprotein As A Predictor Of Outcome In Patients With Unstable Coronary Artery Disease," *Int J Cardiol*. (not yet in print); Epub ahead of print Dec. 7, 2005.

Griffin ME, McInerney D, Fraser A, Johnson AH, Collins PB, Owens D, Tomkin GH. "Autoantibodies to Oxidized Low Density Lipoprotein: the Relationship to Low Density Lipoprotein Fatty Acid Composition in Diabetes." *Diabetic Medicine* (1997), vol. 14, pp. 741-747.

Liu K, Cuddy TE, Pierce GN. "Oxidative status of lipoproteins in coronary disease patients." *American Heart Journal* (1992), vol. 123, pp. 285-290.

Palinski W, Horkko S, Miller E, Steinbrecher UP, Powell HC, Curtiss LK, Witzlum JL. "Cloning of Monoclonal Autoantibodies to Epitopes of Oxidized Lipoproteins from Apolipoprotein E-deficient Mice." *Journal of Clinical Investigation* (1996), vol. 98, pp. 800-814.

Schier R, McCall A, Adams GP, Marshall KW, Merritt H, Yim M, Crawford RS, Weiner LM, Marks C, Marks JD. "Isolation of Picomolar Affinity Anti-c-erbB-2 Single-chain Fv by Molecular Evolution of the Complementary Determining Regions in the Center of the Antibody Binding Site." *Journal of Molecular Biology* (1996), vol. 263, pp. 551-567.

Winzor DJ, De Jersey J. "Biospecific Interactions: Their Quantitative Characterization And Use For Solute Purification." *Journal of Chromatography* (1989), vol. 492, pp. 377-430.

\* cited by examiner

DETECTION AND DETERMINATION OF THE STAGES OF CORONARY ARTERY DISEASE

RELATED APPLICATIONS

This is a divisional of U.S. patent application Ser. No. 10/174,797, filed Jun. 18, 2002 (U.S. Pat. No. 7,166,469), which is a continuation of U.S. patent application Ser. No. 09/906,560, filed Jul. 16, 2001 (abandoned), which is a continuation of U.S. patent application Ser. No. 09/148,158, filed Sep. 4, 1998 (U.S. Pat. No. 6,309,888), and all benefit of those earlier applications (all of which are hereby incorporated in their entireties for all purposes), including under 35 U.S.C. § 120, is hereby claimed.

BACKGROUND OF THE INVENTION

The present invention relates to the field of coronary artery disease. More specifically, it relates to detecting with a clinically sufficient degree of diagnostic accuracy whether a human patient from the general population has coronary artery disease ("CAD") and, if so, to determining with a clinically sufficient degree of diagnostic accuracy which stage of CAD the patient has.

Steinberg D, "Lewis A. Conner Memorial Lecture, Oxidative Modification Of LDL And Atherogenesis," *Circulation* 1997, 95: 1062-1071, notes that deaths from coronary heart disease continue to outnumber deaths from any other single cause in the United States. Kolata, "A New Generation Of Tests To Determine Heart Trouble," *New York Times News Service* (Nov. 26, 1995), reports that half of the 600,000 Americans who have heart attacks each year have no symptoms beforehand and that as many as 30% of heart disease patients do not have any obvious risk factors such as high blood pressure, high cholesterol levels, diabetes, or a family history of heart disease. (All of the documents mentioned or otherwise referenced herein are incorporated herein in their entireties for all purposes.)

The ability to accurately determine whether a patient has coronary artery disease and, if so, what stage the patient has, has been a long-standing (but heretofore unachieved) goal of medical science. There have been many attempts to provide monoclonal antibodies that recognize in humans and other animals various low density lipoprotein ("LDL") substances and/or other substances that might be associated with atherosclerosis and/or thrombosis. There have also been attempts to provide methods for determining possible markers for atherosclerosis and coronary injury. See, e.g., U.S. Pat. Nos. 5,024,829, 5,026,537, 5,120,834, 5,196,324, 5,223,410, 5,362,649, 5,380,667, 5,396,886, 5,453,359, 5,487,892, 5,597,726, 5,658,729, 5,690,103, and 5,756,067; EPO Published Application 0 484 863 A1; PCT/EP97/03287 (unpublished application); PCT/EP97/03493 (unpublished application); PCT Published Application WO 94/23302; Adams et al., "Cardiac Troponin I. A Marker With High Specificity For Cardiac Injury," *Circulation* 1993; 88(1): 101-106; American Biogenetic Sciences Inc., 1995 *Annual Report*, 24 pages (1995); *American Biogenetic Sciences, Focus on Diagnostic Tests: A Technology Analysis, Updated Full Report*, Paisley and Habermas, Inc. (Jun. 3, 1996); Antman et al., "Cardiac-Specific Troponin I Levels To Predict The Risk Of Mortality In Patients With Acute Coronary Syndromes," *N. Eng. J. Med.* 1996; 335(18): 1342-1349; AtheroGenics, Inc. Web Site (WWW.ATHEROGENICS.COM); Hamm et al., "Emergency Room Triage Of Patients With Acute Chest Pain By Means Of Rapid Testing For Cardiac Troponin T Or Troponin I," *N. Eng. J. Med.* 1997; 337(23): 1648-1653; Hammer et al., "Generation, Characterization, And Histochemical Application Of Monoclonal Antibodies Selectively Recognizing Oxidatively Modified ApoB-Containing Serum Lipoproteins," *Arterioscler. Thromb. Vasc. Biol.* 1995; 15(5): 704-713; Hoff et al., "Lesion-Derived Low Density Lipoprotein And Oxidized Low Density Lipoprotein Share A Lability For Aggregation, Leading To Enhanced Macrophage Degradation," *Arterioscler. Thromb.* 1991; 11(5): 1209-1222; Hoffmeister et al., "Alterations Of Coagulation And Fibrinolytic And Kallikrein-Kinin Systems In The Acute And Post-Acute Phases In Patients With Unstable Angina Pectoris," *Circulation* 1995; 91(10): 2520-2527; Holvoet, Collen, et al., "Stimulation With A Monoclonal Antibody (mAb4E4) Of Scavenger Receptor-Mediated Uptake Of Chemically Modified Low Density Lipoproteins By THP-1-Derived Macrophages Enhances Foam Cell Generation," *J. Clin. Invest.* 1994; 93: 89-98; Holvoet and Collen, "β-VLDL Hypercholesterolemia Relative To LDL Hypercholesterolemia Is Associated With Higher Levels Of Oxidized Lipoproteins And A More Rapid Progression Of Coronary Atherosclerosis In Rabbits," *Arterioscler. Thromb. Vasc. Biol.* November 1997; 17(11): 2376-2382; Holvoet and Collen, "Oxidized Lipoproteins In Atherosclerosis And Thrombosis," *FASEB J* 1994; 8: 1279-1284; Holvoet and Collen, "Malondialdehyde-Modified Low Density Lipoproteins In Patients With Atherosclerotic Disease," *J. Clin. Invest.* 1995; 95: 2611-2619; Holvoet, Collen, et al., "Correlation Between Oxidized Low Density Lipoproteins And Von Willebrand Factor In Chronic Renal Failure," *Thromb. Haemost.* 1996; 76(5): 663-669; Holvoet, Collen, et al., "Correlation Between Oxidized Low Density Lipoproteins And Coronary Artery Disease In Heart Transplant Patients,"Abstract published in *Final Programme* of 66th Congress of the European Atherosclerosis Society, Florence (Italy), Jul. 13-14, 1996, *Abstract Book*, page 47; Holvoet, Collen, et al., "Oxidized Low Density Lipoproteins In Patients With Transplant-Associated Coronary Artery Disease," *Arterioscler. Thromb. Vasc. Biol.* January 1998; 18(1): 100-107; Holvoet, Collen, et al., Presentation at 70th Scientific Session Of The American Heart Association, Orlando, Fla., November 9-12, and published in abstract form in *Circulation* 1997; 96(Suppl. I): I417 (Abstract 2328); Itabe et al., "A Monoclonal Antibody Against Oxidized Lipoprotein Recognizes Foam Cells In Atherosclerotic Lesions: Complex Formation Of Oxidized Phosphatidylcholines And Polypeptides," *J. Biol. Chem.* 1994; 269(21): 15274-15279; Itabe et al., "Sensitive Detection Of Oxidatively Modified Low Density Lipoprotein Using A Monoclonal Antibody," *J. Lipid Res.* 1996; 37: 45-53; Kolata, "A New Generation Of Tests To Determine Heart Trouble," *New York Times News Service* (Nov. 26, 1995); Kotani et al., "Distribution Of Immunoreactive Malondialdehyde-Modified Low-Density Lipoprotein In Human Serum," *Biochimica et Biophysica Acta* 1994; 1215: 121-125; Menschikowski et al., "Secretory Group II Phospholipase A2 In Human Atherosclerotic Plaques," *Atherosclerosis* 1995; 118:173-181; Muldoon et al., "C-Reactive Protein And Serum Amyloid A Protein In Unstable Angina," *N. Engl. J. Med.* 1995; 332(6): 398-400; Ohman et al., "Cardiac Troponin T Levels For Risk Stratification In Acute Myocardial Ischemia," *N. Eng. J. Med.* 1996 335(18): 1333-1341; Palinski et al., "Antisera And Monoclonal Antibodies Specific For Epitopes Generated During Oxidative Modification Of Low Density Lipoprotein," *Arteriosclerosis* 1990; 10(3): 325-335; Ravalli et al., "Immunohistochemical Demonstration Of 15-Lipoxygenase In Transplant Coronary Artery Disease," *Arterioscler. Thromb. Vasc. Biol.* 1995; 15(3): 340-348; Reade et al., "Expression Of Apolipoprotein B Epitopes In Low Density Lipoproteins Of Hemodialyzed Patients," *Kid-* ney Int. 1993; 44: 1360-1365; Reverter et al., "Platelet Activation During Hemodialysis Measured Through Exposure Of P-Selectin: Analysis By Flow Cytometric And Ultrastructural Techniques," *J. Lab. Clin. Med.* 1994; 124(1): 79-85; Salonen et al., "Autoantibody Against Oxidised LDL And Progression Of Carotid Atherosclerosis," *Lancet* 1992; 339(8798): 883-887; Uchida et al., "Protein-Bound Acrolein: Potential Markers For Oxidative Stress," *Proc. Natl. Acad. Sci. USA* 1998; 95: 4882-4887; and Van de Werf, "Cardiac Troponins In Acute Coronary Syndromes," *N. Eng. J. Med.* 1996; 335(18): 1388-1389.

However, as noted in the literature, there is no currently available method for determining with a clinically sufficient degree of diagnostic accuracy the presence of coronary artery disease in a patient and, if the disease is present, for distinguishing with a clinically sufficient degree of diagnostic accuracy between or among the non-acute (i.e., chronic) and acute stages of that disease, the non-acute stages being stable angina and presumably asymptomatic coronary artery disease and the acute stages being unstable angina and acute myocardial infarction.

For example, U.S. Pat. No. 5,380,667 (issued Jan. 10, 1995) notes that most individuals with heart disease are largely asymptomatic until their first heart attack, that the major risk factors thus far identified in the prior art are not perfect predictors (particularly for predicting the risk of coronary artery disease in any single individual), and that thirty to forty percent of the population is still misdiagnosed using the known major risk factors (column 1, lines 31-39).

Hlatky M A, "Evaluation Of Chest Pain In The Emergency Department," *N. Eng. J. Med.* December 1997, 337(23): 1687-1689, reports that after patients in the emergency department having clear-cut acute myocardial infarction have been identified, the remaining patients are more difficult to sort out; that symptoms suggestive of myocardial ischemia at rest that last more than 15 minutes indicate a relatively high short-term risk, probably because of their association with ruptured coronary plaque; that further tests used for patients include those that identify a defect in myocardial perfusion, abnormalities in left ventricular wall motion, or subtle evidence of myocardial necrosis though sensitive assays of intracellular proteins (e.g., CK-MB isoenzyme, myoglobin, troponin T, and troponin I); that even a highly sensitive marker of myocardial necrosis will not necessarily be positive in all patients with acute myocardial ischemia; and that patients who present for the first time with chest pain usually need further tests to establish the likelihood of underlying coronary disease and to guide appropriate therapy.

U.S. Pat. No. 5,756,067 (issued May 26, 1998) notes that tests currently available to measure the risk of developing atherosclerosis include measuring the plasma content of cholesterol, triglycerides, and lipoproteins but that it is clear that these tests are not conclusive because approximately one-half of heart disease due to atherosclerosis occurs in patients with plasma triglycerides and cholesterol within the normal ranges of the population and because angiographic evidence of atherosclerosis has been found in patients with normal lipid levels.

Sasavage N, "Predicting Coronary Artery Disease, New Markers Could Identify Patients At Risk," *Clin. Lab. News* March 1998, pages 6-7, suggests that oxidation of low density lipoproteins may render it more atherogenic, that detection of oxidized LDL species faces some technical difficulties, and indicates that coronary artery disease appears to be a multifactorial disease. It also states that those who work in this area agree that development of a new generation of biochemical markers will allow clinicians to better assess patient risk and intervene with treatments to avoid adverse outcomes.

Thus, there is a significant need for a method that with a clinically sufficient degree of diagnostic accuracy can detect coronary artery disease and distinguish between or among its stages.

SUMMARY OF THE INVENTION

An invention satisfying those needs and having advantages and benefits that will be apparent to one skilled in the art has now been developed. Broadly, this invention provides a method having a clinically sufficient degree of diagnostic accuracy for detecting the presence of and for distinguishing between or among the non-acute and the acute stages of coronary artery disease for a human patient from the general population, the non-acute stage of coronary artery disease being either asymptomatic coronary artery disease or stable angina and the acute stages of coronary artery disease being unstable angina and acute myocardial infarction, the method comprising performing step (b) and performing at least one of steps (a) and (c):

(a) testing a sample from the patient for a clinically significant presence of a first marker whose presence above a predetermined level can indicate with a very high degree of diagnostic accuracy the presence of coronary artery disease;

(b) testing a sample from the patient for a clinically significant presence of second marker whose presence above a predetermined level can indicate with a very high degree of diagnostic accuracy the presence of an acute stage of coronary artery disease; and (c) testing a sample from the patient for a clinically significant presence of a third marker whose presence above a predetermined level can indicate with a high degree of diagnostic accuracy the presence of acute myocardial infarction.

In some embodiments of the invention, steps (a) and (b) but not (c) will be used, in other embodiments steps (b) and (c) but not (a) will be used, and in still other embodiments all three of steps (a), (b), and (c) will be used.

In some embodiments, the first marker is a first atherogenic protein preferably comprising OxLDL containing at least 60 substituted lysine residues per apo B-100 moiety. In some embodiments, the second marker is a second atherogenic protein preferably comprising MDA-modified LDL containing at least 60 substituted lysine residues per apo B-100 moiety. In some embodiments, the third marker is a heart protein and preferably is a troponin (e.g., Troponin I) or CK-MB.

Desirably each of steps (a) and (b) uses an immunological assay, which is preferably a sandwich assay, although a competitive assay may be used. Preferably, each immunological assay uses one or more monoclonal antibody having high affinities for their respective markers, e.g., affinity of at least about $1\times10^{10}$ $M^{-1}$. ("M" indicates molarity or gmoles/liter; "$M^{-1}$" indicates the reciprocal of molarity, or liters per mole.) The monoclonal antibodies used may be selected from the group consisting of mAb-4E6, mAb-1H11, and mAb-8A2.

If the marker of step (a) is OxLDL containing at least 60 substituted lysine residues per apo B-100 moiety, preferably the test used in step (a) is capable of detecting that substance in undiluted human plasma in a concentration of 0.02 milligrams/deciliter (0.02 mg/dL). If the marker of step (b) is MDA-modified LDL containing at least 60 substituted lysine residues per apo B-100 moiety, preferably the test used in step (b) is capable of detecting that substance in undiluted human plasma in a concentration of 0.02 milligrams/deciliter (0.02 mg/dL).

In another aspect, this invention provides a method having a clinically sufficient degree of diagnostic accuracy for detecting the presence of and for distinguishing between or among the non-acute and the acute stages of coronary artery disease for a human patient from the general population, the non-acute stage of coronary artery disease being either asymptomatic coronary artery disease or stable angina and the acute stages of coronary artery disease being unstable angina and acute myocardial infarction, the method comprising the steps:

(a) testing a sample from the patient using an immunological assay for a clinically significant presence of OxLDL containing at least 60 substituted lysine residues per apo B-100 moiety, its presence above a predetermined level being able to indicate with a very high degree of diagnostic accuracy the presence of coronary artery disease, the assay employing at least one monoclonal antibody having a high affinity for the OxLDL;

(b) testing a sample from the patient using an immunological assay for a clinically significant presence of MDA-modified LDL containing at least 60 substituted lysine residues per apo B-100 moiety, its presence above a predetermined level being able to indicate with a very high degree of diagnostic accuracy the presence of an acute stage of coronary artery disease, the assay employing at least one monoclonal antibody having a high affinity for MDA-modified LDL; and (c) optionally testing a sample from the patient for a clinically significant presence of a third marker whose presence above a predetermined level can indicate with a high degree of diagnostic accuracy the presence of acute myocardial infarction.

In yet another aspect, this invention provides a method having a clinically sufficient degree of diagnostic accuracy for detecting the presence of and for distinguishing between or among the non-acute and the acute stages of coronary artery disease for a human patient from the general population, the non-acute stage of coronary artery disease being either asymptomatic coronary artery disease or stable angina and the acute stages of coronary artery disease being unstable angina and acute myocardial infarction, the method comprising the steps:

(a) testing a sample from the patient using an immunological assay for a clinically significant presence of OxLDL containing at least 60 substituted lysine residues per apo B-100 moiety, its presence above a predetermined level being able to indicate with a very high degree of diagnostic accuracy the presence of coronary artery disease, the assay employing at least one monoclonal antibody having a high affinity for the OxLDL;

(b) testing a sample from the patient using an immunological assay for a clinically significant presence of MDA-modified LDL containing at least 60 substituted lysine residues per apo B-100 moiety, its presence above a predetermined level being able to indicate with a very high degree of diagnostic accuracy the presence of an acute stage of coronary artery disease, the assay employing at least one monoclonal antibody having a high affinity for MDA-modified LDL; and (c) testing a sample from the patient for a clinically significant presence of a heart protein whose presence above a predetermined level can indicate with a high degree of diagnostic accuracy the presence of acute myocardial infarction.

The clinically significant presence (presence above a predetermined level) of the first marker (e.g., OxLDL having at least at least 60 substituted lysine residues per apo B-100 moiety) can indicate with a very high degree of diagnostic accuracy the presence of coronary artery disease. In other words, the test or assay of this invention used for detecting a marker of coronary artery disease will distinguish with a very high degree of diagnostic accuracy between the following categories 1 and 2: (1) those who do not have coronary artery disease and (2) those who do have one of the categories or stages of coronary artery disease (i.e., those who have non-acute [or chronic] disease, namely, stable angina or presumably asymptomatic coronary artery disease, or those who have acute coronary syndromes clinically presenting as unstable angina or acute myocardial infarction), but by itself will generally not be able to distinguish between the categories (or stages) of coronary artery disease.

The clinically significant presence (presence above a predetermined level) of the second marker (e.g., MDA-modified LDL having at least at least 60 substituted lysine residues per apo B-100 moiety) can indicate with a very high degree of diagnostic accuracy the presence of an acute stage of coronary artery disease. In other words, the test or assay of this invention for detecting a marker of an acute stage of coronary artery disease will distinguish between the following categories 1 and 2: (1) those who do not have an acute stage of coronary artery disease (i.e., those who have either (a) no coronary artery disease or have non-acute coronary artery disease, namely, (b) asymptomatic coronary artery disease or (c) stable angina) but by itself will generally not be able to distinguish between those three categories a, b, and c, and (2) those who do have one of the two categories or stages of acute coronary artery disease (i.e., those who have either (a) unstable angina or (b) acute myocardial infarction) but by itself will generally not be able to distinguish between the two acute categories.

The clinically significant presence (presence above a predetermined level) of the third marker (e.g., CK-MB or a troponin) can indicate with a high degree of diagnostic accuracy the presence of acute myocardial infarction. In other words, the test or assay of this invention for detecting a marker of acute myocardial infarction will distinguish between the following categories 1 and 2: (1) those who have acute myocardial infarction and (2) those who do not (i.e., those who have no coronary artery disease, those who have non-acute coronary artery disease, namely, stable angina or presumably asymptomatic coronary artery disease, and those who have unstable angina) but by itself will generally not be able to distinguish between the non-AMI categories.

Use of the first and second tests (assays) together on a patient will allow the patient to be put with a clinically sufficient degree of diagnostic accuracy into one of three categories: (1) having no coronary artery disease (first and second tests negative); (2) having coronary artery disease of the non-acute type, i.e., either asymptomatic coronary artery disease or stable angina (first test positive, second test negative); or (3) having coronary artery disease of the acute type, i.e., either unstable angina or acute myocardial infarction (both tests positive). The first and second tests may be used together, for example, as part of a screening or as part of a routine physical examination. If the patient is put in the first category, there is no problem. If the patient is put in the second category, the physician may take action such as recommending a change in life style, prescribing appropriate medication, etc. That is particularly true for asymptomatic CAD patients, who will be placed in the second category, and who may not have had any previous indication of coronary artery disease. If the patient is put in the category of acute coronary disease, the third test of this invention may be run to determine whether the patient has had or is having an acute myocardial infarction and, if that is the case, the physician may recommend immediate hospitalization and medication (e.g., tissue plasminogen activator, "TPA").

Use of the second and third tests (assays) on a patient without the first test also being run will likely occur less frequently than use of the first and second tests without the third test. However, for a patient who has acute symptoms that suggest an acute myocardial infarction (e.g., chest pain), the physician may run the third test to determine if the patient is in fact having an acute myocardial infarction (in which case the third test, e.g., for a troponin, would likely be positive) and will likely also want to run the second test to determine whether the acute myocardial infarction, if present, is most likely caused by coronary atherosclerosis (the second test, e.g., for MDA-modified LDL, would be positive) or if the acute myocardial infarction likely results from some other cause. For patients presenting classical symptoms of acute myocardial infarction, use of the second and third tests together is highly advantageous and the first test might not be needed in the first instance or at all.

Thus, in accordance with this invention, if all three tests are run on a patient, the patient may be placed into one of the following categories with a clinically sufficient degree of diagnostic accuracy: (1) having no CAD; (2) having non-acute (chronic) CAD, namely, either asymptomatic or stable angina; (3) having the first form of acute CAD, namely, unstable angina; and (4) having the second form of acute CAD, namely, (a) acute myocardial infarction ("AMI") that is likely due to atherosclerosis and (b) AMI that is likely due to a cause other than atherosclerosis. Categories 2, 3, and 4 may be thought of as being the stages of coronary artery disease (CAD).

The clinically significant presence of a first marker in a sample from a patient (first assay is positive) indicates that the patient is not in category 1 (no CAD) and is either in category 2 (asymptomatic CAD or stable angina) or 3 (unstable angina) or 4 (AMI). In other words, the clinically significant presence of the first marker in a sample from the patient indicates that the patient has coronary artery disease. If the first marker does not have clinically significant presence in the sample (first assay is negative), the patient is in category 1, in other words, does not have CAD. If the assay for the first marker is negative and the assay for the second marker is positive, it indicates a likely problem with one or both of the assays because that pairing of test results is highly unlikely, and one or both tests should be repeated. Thus, another beneficial feature of the invention is that by using the first and second assays together, a positive first assay will confirm a positive second assay, and a negative first assay will cast significant doubt about a positive second assay and will thereby indicate a likely problem with one or both assays.

The clinically significant presence of the first marker in a sample from a patient coupled with the clinically significant presence of the second marker in a sample from the patient indicates that the patient is not in category 1 (no CAD) or 2 (asymptomatic CAD or stable angina) and is instead in category 3 (unstable angina) or category 4 (AMI). If neither the first nor the second marker has a clinically significant presence, the patient is in category 1, in other words, does not have CAD.

The clinically significant presence of the first marker in a sample from a patient, coupled with the clinically significant presence of the second marker in a sample from the patient, coupled with the clinically significant presence of the third marker in a sample from the patient indicates that the patient is not in category 1 (no CAD) or 2 (asymptomatic CAD or stable angina) or 3 (unstable angina) and is instead in category 4 (AMI). If the first and second and third markers do not have clinically significant presence, the patient is in category 1, in other words, does not have CAD. If the first and second assays are negative but the third assay is positive, it indicates AMI caused by something other than coronary atherosclerotic disease. If the second and third assays are positive and the first assay is not run (e.g., for a patient presenting classic AMI symptoms), the patient is in category 4 and the positive second assay indicates that the heart damage is likely caused by coronary atherosclerotic disease. If the first test is negative but the second is positive, the results are equivocal and it may indicate, e.g., a possible problem with one or more of the tests. If the first and third tests are positive but the second is negative, the results are equivocal and it may indicate, e.g., a possible problem with the tests or a possible non-atherosclerotic AMI.

Table I, below, summarizes the possible test outcomes and resulting categorizations (diagnoses) using the method of this invention (a plus sign indicates that the test for that marker is positive; a negative sign indicates that the test for that marker is negative):

TABLE I

| Category | First Marker | Second Marker | Third Marker |
|---|---|---|---|
| No CAD | − | − | − |
| Chronic CAD | + | − | − |
| Unstable Angina | + | + | − |
| AMI (atherosclerotic) | + | + | + |
| AMI (non-atherosclerotic) | − | − | + |
| Equivocal | − | + | − |
| Equivocal | − | + | + |
| Equivocal | + | − | + |

The "diagnostic accuracy" of a test, assay, or method concerns the ability of the test, assay, or method to distinguish between patients having a disease, condition, or syndrome and patients not having that disease, condition, or syndrome based on whether the patients have a "clinically significant presence" of an analyte. By "clinically significant presence" is meant that the presence of the analyte (e.g., mass, such as milligrams or nanograms, or mass per volume, such as milligrams per deciliter) in the patient (typically in a sample from the patient) is higher than the predetermined cut point (or threshold value) for that analyte and therefore indicates that the patient has the disease, condition, or syndrome for which the sufficiently high presence of that analyte is a marker.

The terms "high degree of diagnostic accuracy" and "very high degree of diagnostic accuracy" refer to the test or assay for that analyte with the predetermined cut point correctly (accurately) indicating the presence or absence of the disease, condition, or syndrome. A perfect test would have perfect accuracy. Thus, for individuals who have the disease, condition, or syndrome, the test would indicate only positive test results and would not report any of those individuals as being "negative" (there would be no "false negatives"). In other words, the "sensitivity" of the test (the true positive rate) would be 100%. On the other hand, for individuals who did not have the disease, condition, or syndrome, the test would indicate only negative test results and would not report any of those individuals as being "positive" (there would be no "false positives"). In other words, the "specificity" (the true negative rate) would be 100%. See, e.g., O'Marcaigh A S, Jacobson R M, "Estimating The Predictive Value Of A Diagnostic Test, How To Prevent Misleading Or Confusing Results," *Clin. Ped.* 1993, 32(8): 485-491, which discusses specificity, sensitivity, and positive and negative predictive values of a test, e.g., a clinical diagnostic test.

Changing the cut point or threshold value of a test (or assay) usually changes the sensitivity and specificity but in a qualitatively inverse relationship. For example, if the cut point is lowered, more individuals in the population tested will typically have test results over the cut point or threshold value. Because individuals who have test results above the cut point are reported as having the disease, condition, or syndrome for which the test is being run, lowering the cut point will cause more individuals to be reported as having positive results (i.e., that they have the disease, condition, or syndrome). Thus, a higher proportion of those who have the disease, condition, or syndrome will be indicated by the test to have it. Accordingly, the sensitivity (true positive rate) of the test will be increased. However, at the same time, there will be more false positives because more people who do not have the disease, condition, or syndrome (i.e., people who are truly "negative") will be indicated by the test to have analyte values above the cut point and therefore to be reported as positive (i.e., to have the disease, condition, or syndrome) rather than being correctly indicated by the test to be negative. Accordingly, the specificity (true negative rate) of the test will be decreased. Similarly, raising the cut point will tend to decrease the sensitivity and increase the specificity. Therefore, in assessing the accuracy and usefulness of a proposed medical test, assay, or method for assessing a patient's condition, one should always take both sensitivity and specificity into account and be mindful of what the cut point is at which the sensitivity and specificity are being reported because sensitivity and specificity may vary significantly over the range of cut points.

There is, however, an indicator that allows representation of the sensitivity and specificity of a test, assay, or method over the entire range of cut points with just a single value. That indicator is derived from a Receiver Operating Characteristics ("ROC") curve for the test, assay, or method in question. See, e.g., Shultz, "Clinical Interpretation Of Laboratory Procedures," chapter 14 in *Teitz, Fundamentals of Clinical Chemistry*, Burtis and Ashwood (eds.), 4th edition 1996, W.B. Saunders Company, pages 192-199; and Zweig et al., "ROC Curve Analysis: An Example Showing The Relationships Among Serum Lipid And Apolipoprotein Concentrations In Identifying Patients With Coronary Artery Disease," *Clin. Chem.*, 1992, 38(8): 1425-1428.

An ROC curve is an x-y plot of sensitivity on the y-axis, on a scale of zero to one (i.e., 100%), against a value equal to one minus specificity on the x-axis, on a scale of zero to one (i.e., 100%). In other words, it is a plot of the true positive rate against the false positive rate for that test, assay, or method. To construct the ROC curve for the test, assay, or method in question, patients are assessed using a perfectly accurate or "gold standard" method that is independent of the test, assay, or method in question to determine whether the patients are truly positive or negative for the disease, condition, or syndrome (for example, coronary angiography is a gold standard test for the presence of coronary atherosclerosis). The patients are also tested using the test, assay, or method in question, and for varying cut points, the patients are reported as being positive or negative according to the test, assay, or method. The sensitivity (true positive rate) and the value equal to one minus the specificity (which value equals the false positive rate) are determined for each cut point, and each pair of x-y values is plotted as a single point on the x-y diagram. The "curve" connecting those points is the ROC curve.

The area under the curve ("AUC") is the indicator that allows representation of the sensitivity and specificity of a test, assay, or method over the entire range of cut points with just a single value. The maximum AUC is one (a perfect test) and the minimum area is one half. The closer the AUC is to one, the better is the accuracy of the test.

By a "high degree of diagnostic accuracy" is meant a test or assay (such as the test of the invention for determining the clinically significant presence of the third analyte, which thereby indicates the presence of an acute myocardial infarction) in which the AUC (area under the ROC curve for the test or assay) is at least 0.70, desirably at least 0.75, more desirably at least 0.80, preferably at least 0.85, more preferably at least 0.90, and most preferably at least 0.95.

By a "very high degree of diagnostic accuracy" is meant a test or assay (such as the test of the invention for determining the clinically significant presence of the first analyte, which thereby indicates the presence of coronary artery disease, or the test for determining the clinically significant presence of the second analyte, which thereby indicates the presence of an acute stage of coronary artery disease) in which the AUC (area under the ROC curve for the test or assay) is at least 0.875, desirably at least 0.90, more desirably at least 0.925, preferably at least 0.95, more preferably at least 0.975, and most preferably at least 0.98.

By a "clinically sufficient degree of diagnostic accuracy" is meant a method (such as the method of the invention) that (1) in a first test can assay for a first marker whose presence above a predetermined level can indicate with a very high degree of diagnostic accuracy the presence of coronary artery disease, (2) in a second test can assay for a second marker whose presence above a predetermined level can indicate with a very high degree of diagnostic accuracy the presence of an acute stage of coronary artery disease, and (3) in a third test can assay for a third marker whose presence above a predetermined level can indicate with a high degree of diagnostic accuracy the presence of acute myocardial infarction; wherein at least the second test is run and either or both of the first and third tests are run.

The method of the present invention provides a degree of clinical diagnostic accuracy for detecting the presence of and for distinguishing between or among the non-acute (chronic) and the acute stages of coronary artery disease for a human patient from the general population that is that is significantly higher than any other previously known method. However, the advantages of this invention include not just the high overall accuracy made possible by its tests but that the use of the tests together rapidly provides all the information needed by the clinician about the patient to permit possible life-saving treatment. Thus, the physician will know by using the method of this invention for a specific patient that the patient does not have coronary artery disease; or, if the presence of the disease is already known, that the measures being taken to deal with it are either adequate or inadequate; or that patient has the disease but did not know it and that a change in diet and/or exercise habits and/or medication and/or other treatment are needed, but not on an emergency basis; or that the patient has a life-threatening coronary problem and must be dealt with on an emergency basis. Another advantage is that acute myocardial infarctions due to coronary atherosclerosis can be distinguished from those due to other causes, which knowledge will significantly affect treatment. Yet another advantage is that in some cases the tests will act to confirm the validity of each other and thereby give the physician more confidence in diagnosis and treatment.

DETAILED DESCRIPTION OF THE INVENTION

Lipoproteins are multicomponent complexes of protein and lipids. Each type of lipoprotein has a characteristic molecular weight, size, chemical composition, density, and physical role. The protein and lipid are held together by noncovalent forces.

Lipoproteins can be classified on the basis of their density as determined by ultracentrifugation. Thus, four classes of lipoproteins can be distinguished: High Density Lipoproteins ("HDL"), Intermediate Density Lipoproteins ("IDL"), Low Density Lipoproteins ("LDL"), and Very Low Density Lipoproteins ("VLDL").

The purified protein components of a lipoprotein particle are called apolipoproteins (apo). Each type of lipoprotein has a characteristic apolipoprotein composition. In LDL the prominent apolipoprotein protein is apo B-100, which is one of the longest single chain polypeptides known and consists of 4536 amino acids. Of these amino acids the lysine residues or moieties (there are 356 such lysine residues or moieties) can be substituted or modified by aldehydes (e.g., malondialdehyde).

Oxidation of the lipids in LDL (whether in vitro, e.g., by copper-induced oxidation, or whether in vivo) results in the generation of reactive aldehydes, which can then interact with the lysine residues or moieties of apo B-100. The outcome of this lysine substitution or modification is that the resulting oxidized low density lipoprotein ("OxLDL"), which is also malondialdehyde-modified low density lipoprotein ("MDA-modified LDL"), is no longer recognized by the LDL receptor at the surface of fibroblasts but by scavenger receptors at the surface of macrophages. At least 60 out of the 356 lysines (or lysine residues or moieties) of apo B-100 have to be substituted in order to be recognized by the scavenger receptors. The uptake of such OxLDL by macrophages results in foam cell generation, which is considered to be an initial step in atherosclerosis.

Endothelial cells under oxidative stress (e.g., in acute myocardial infarction patients) and activated blood platelets also produce aldehydes, which interact with the lysine moieties in apo B-100, resulting in the generation of aldehyde-modified LDL that is also recognized by the scavenger receptors. However, the lipids in this aldehyde-modified LDL are not oxidized. Enzymatic activity in macrophages (e.g., myeloperoxidase) results in the oxidation of both the lipid and the protein moieties of LDL. All these pathways result in aldehyde-type modification of the protein moiety of LDL.

The first marker can be any marker whose clinically significant presence indicates with a very high degree of diagnostic accuracy the presence of coronary artery disease. Desirably, the first marker is an atherogenic protein. Preferably, the atherogenic protein comprises OxLDL containing at least 60, desirably up to about 90, more desirably up to about 120, preferably up to about 180, more preferably up to about 210, and most preferably possibly up to about 240 substituted lysine residues per apo B-100 moiety.

The second marker can be any marker whose clinically significant presence indicates with a very high degree of diagnostic accuracy the presence of an acute stage of coronary artery disease. Desirably, the second marker is an atherogenic protein. Preferably, the atherogenic protein comprises MDA-modified LDL containing at least 60, desirably up to about 90, more desirably up to about 120, preferably up to about 180, more preferably up to about 210, and most preferably possibly up to about 240 substituted lysine residues per apo B-100 moiety.

The third marker can be any marker whose clinically significant presence indicates with a high degree of diagnostic accuracy the presence of acute myocardial infarction. The gold standard chemical marker for acute myocardial infarction has been CK-MB but may be shifting to the troponins (e.g., troponin I, troponin T). See, e.g., Adams et al., "Cardiac Troponin I, A Marker With High Specificity For Cardiac Injury," Circulation 1993,88(1): 101-106; Antman et al., "Cardiac-Specific Troponin I Levels To Predict The Risk Of Mortality In Patients With Acute Coronary Syndromes," N. Eng. J. Med. 1996, 335(18): 1342-1349; Hamm et al., "Emergency Room Triage Of Patients With Acute Chest Pain By Means Of Rapid Testing For Cardiac Troponin T Or Troponin I," N. Eng. J. Med. 1997, 337(23): 1648-1653; Ohman et al., "Cardiac Troponin T Levels For Risk Stratification In Acute Myocardial Ischemia," N. Eng. J. Med. 1996, 335(18): 1333-1341; and Van de Werf, "Cardiac Troponins In Acute Coronary Syndromes," N. Eng. J. Med. 1996, 335(18): 1388-1389. Another substance that may possibly be used as the third marker is a marker for active or incipient coronary thrombosis. Thus, a "marker whose presence above a predetermined level can indicate with a high degree of diagnostic accuracy the presence of acute myocardial infarction" should be understood to include markers of active and incipient coronary thrombosis even before substances indicative of cardiac tissue damage or death have been formed and/or released. Generally speaking, the third marker will typically be a "heart protein," which as used herein means a protein (e.g., an enzyme) that is produced as a result of or is otherwise associated with ischemic damage to the heart or that is a precursor or derivative of that protein.

Testing for the clinically significant presence of the markers may use any assays, methodology, and equipment provided the benefits of this invention can be achieved, e.g., chemical assays and immunological assays, such as competitive and sandwich assays, may be used. "Competitive assays" are well-known and any competitive assay may be used in this invention provided the benefits of the invention can be achieved. "Sandwich assays" are well-known and any sandwich assay may be used in this invention provided the benefits of the invention can be achieved.

In an immunological assay, any antibodies that have suitably high affinity for the target species may be used, and preferably the antibodies are monoclonal antibodies. As used herein, "high affinity" means an affinity constant (association constant) of at least about $5 \times 10^8$ $M^{-1}$ (where "M" indicate molarity or moles per liter, and "$M^{-1}$" indicates reciprocal molarity or liters per mole), desirably of at least about $1 \times 10^9$ $M^{-1}$, preferably of at least about $1 \times 10^{10}$ $M^{-1}$, and most preferably of at least about $1 \times 10^{11}$ $M^{-1}$. As used herein, "low affinity" (in contradistinction to high affinity) means an affinity constant (association constant) of less than about $1 \times 10^7$ $M^{-1}$, desirably less than about $1 \times 10^6$ $M^{-1}$, and preferably less than about $1 \times 10^5$ $M^{-1}$. Affinity constants are determined in accordance with the appropriate method described in Holvoet, Collen, et al., J. Clin. Invest. 1994, 93: 89-98.

The preferred antibodies used in this first and second assays of this invention will bind with OxLDL and/or MDA-modified LDL whose apo B-100 moieties contain at least 60, desirably up to about 90, more desirably up to about 120, preferably up to about 180, more preferably up to about 210, and most preferably possibly up to about 240 substituted lysine residues per apo B-100 moiety. The range of lysine substitution will generally be from 60 up to about 240 substituted lysine moieties per apo B-100 moiety and sometimes from 60 up to about 180 substituted lysine moieties per apo B-100 moiety.

Each monoclonal antibody used in the first and second assays is desirably highly specific for a conformational epitope that is present when at least about 60, preferably up to about 120 lysine residues, are substituted and by virtue thereof can distinguish the first and second markers of the first and second assays. Antibodies recognizing epitopes present when less than about 60 lysines per apo B-100 moiety are substituted or modified are less specific but are still useful (e.g., they may be used as the secondary antibody in a sandwich ELISA).

The preferred antibodies used herein are monoclonal antibodies mAb-4E6, mAb-1h11, and mAb-8A2. Their affinity constants for native LDL, MDA-modified LDL, and OxLDL are as follows (the units are liters per mole, which equals the reciprocal of molarity or $M^{-1}$):

TABLE II

| Antibody | Native LDL | MDA-modified LDL | OxLDL |
| --- | --- | --- | --- |
| mAb-4E6 | less than $1 \times 10^6$ | $3 \times 10^{10}$ | $2 \times 10^{10}$ |
| mAb-1H11 | less than $1 \times 10^6$ | $3 \times 10^{10}$ | less than $1 \times 10^6$ |
| mAb-8A2 | $5 \times 10^9$ | $1 \times 10^{10}$ | $1 \times 10^{10}$ |

Monoclonal antibody mAb-4E6 is produced by hybridoma Hyb4E6 deposited at the BCCM under deposit accession number LMBP 1660 CB on or about Apr. 24, 1997. Monoclonal antibody mAb-1H11 is produced by hybridoma Hyb1H11 deposited at the BCCM under deposit accession number LMBP 1659 CB on or about Apr. 24, 1997. Monoclonal antibody mAb-8A2 is produced by hybridoma Hyb8A2 deposited at the BCCM under deposit accession number LMBP 1661 CB on or about Apr. 24, 1997.

The BCCM is the Belgian Coordinated Collections of Microorganisms authorized by the Budapest Treaty Of 28 Apr. 1977 On The International Recognition Of The Deposit Of Microorganisms For The Purpose Of Patent Procedure ("Budapest Treaty"). Its address is c/o The University of Gent, K. L. Ledeganckstraat 35, B-9000 Gent, Belgium.

The three deposits were made at the BCCM under conditions prescribed by the Budapest Treaty. In accordance with The United States Code Of Federal Regulations (see 37 CFR § 1.808) and The United States Patent And Trademark Office's *Manual Of Patent Examination* ("MPEP") (see § 2410.01), all restrictions imposed by the depositor on the availability to the public of the deposited material (except as permitted by the MPEP) will be irrevocably removed upon the granting of any patent issuing from this application or from any continuing application based thereon.

As described elsewhere, those three monoclonal antibodies were obtained in the following way (see PCT Applications PCT/EP97/03287, filed Jun. 20, 1997, and PCT/EP97/03493, filed Jul. 1, 1997 [both designating the United States and other countries, and naming Paul Holvoet and DésiréCollen as inventors, and, as noted above, both of which are incorporated herein in there entireties for all purposes]).

Balb/c mice were immunized by intravenous and intraperitoneal injection of either OxLDL or MDA-modified LDL. OxLDL was obtained by in vitro incubation of LDL (final apo B-100 concentration 700 µg/mL) with copper chloride (final concentration 640 µM) for 16 hours at 37° C. MDA-modified LDL was prepared by incubation of LDL (final apo B-100 concentration 700 µg/mL) with a 0.25 M MDA-solution for 3 hours at 37° C. The numbers of substituted lysines, measured in the TBARS assay, was typically 210 per apo B-100 molecule for OxLDL and 240 for MDA-modified LDL. Hybridomas were obtained by PEG-induced fusion with spleen lymphocytes derived from immunized mice with P3-X63/Ag-6.5.3 myeloma cells according to standard techniques (Holvoet, Collen, et al., *J. Clin. Invest.* 1994; 93: 89-98). The screening for hybridomas producing specific antibodies was performed with ELISA using microtiter plates coated with MDA-modified LDL or copper-oxidized LDL. Three hundred eight hybridomas were obtained after immunization of mice with either OxLDL (211) or MDA-modified LDL (97). Hyb4E6 produced antibodies specific for both MDA-modified and copper-oxidized LDL (mAb-4E6), and Hyb1H11 produced antibodies specific for MDA-modified LDL (mAb-1H11) alone. Mice immunized with LDL in a similar method yielded hybridoma Hyb8A2, which produced antibody mAb-8A2.

The preferred assay is an Enzyme-Linked Immunosorbent Assay ("ELISA"). For example, in the case of a competitive ELISA, a solid substrate coated with OxLDL or MDA-modified LDL may be contacted for a predetermined period of time with the monoclonal antibody mAb-4E6 and a sample thought or known to contain OxLDL and/or MDA-modified LDL, after which period of time unbound antibody and sample are removed and a binding reaction between antibody and OxLDL and/or MDA-modified LDL bound to the substrate is visualized and/or quantified. Quantification in a competitive ELISA is indirect because the binding between the antibody and the analyte in the sample is not measured but instead the amount of antibody that binds to the known amount of OxLDL or MDA-modified LDL that is coated on (bound to) the substrate is measured. The more antibody bound to the known amount of OxLDL or MDA-modified LDL coated on the substrate, the less analyte there was in the sample.

A typical competitive assay using monoclonal antibody mAb-4E6 is as follows. It is based on the inhibition by copper-oxidized LDL of the binding of mAb-4E6 to the coated wells of microtiter plates. Thus, standard OxLDL (or MDA-modified LDL) and plasma samples are diluted in PBS (phosphate buffered saline) containing 1 mM EDTA, 20 µM Vitamin E, 10 µM butylated hydroxytoluene, 20 µM dipyridamole, and 15 mM theophylline to prevent in vitro LDL oxidation and platelet activation. Equal volumes of diluted purified mAb-4E6 solution (final concentration 7.5 ng/mL) and of either diluted standard solution or diluted plasma samples (copper-oxidized LDL added as competing ligand at a final concentration ranging from 50 to 500 ng/mL) are mixed and incubated for 30 min at room temperature. Then 200 µL aliquots of the mixtures are added to wells coated with MDA-modified LDL or OxLDL. The aliquots are incubated for 2 hours at room temperature. After washing, the wells are incubated for 1 h with horse-radish peroxidase conjugated rabbit IgG raised against mouse immunoglobulins and washed again. The peroxidase reaction is performed (see Holvoet, Collen, et al., *J. Clin. Invest.* 1995, 95: 2611-2619) and the absorbance (A) is read at 492 nm. Controls without competing ligand and blanks without antibody may be routinely included. The percent inhibition of binding of mAb-4E6 to the immobilized ligand may be calculated as:

$$\frac{A^{492\,nm}\text{control} - A^{492\,nm}\text{sample}}{A^{492\,nm}\text{control} - A^{492\,nm}\text{blank}}$$

and standard curves may be obtained by plotting the percentage of inhibition against the concentration of competing ligand. The lower limit of detection is 0.020 mg/dL in undiluted human plasma.

In the case of a sandwich ELISA, mAb-4E6 (for MDA-modified LDL and OxLDL) or mAb-1H11 (for MDA-modified LDL) may be bound to a solid substrate and subsequently contacted with a sample to be assayed. After removal of the sample, binding between the specific antibody and OxLDL and/or MDA-modified LDL captured out of the sample can be visualized and/or quantified by detection means. Detection means may be a labeled, less specific secondary antibody that recognizes a different part of the apo B-100 moiety of the captured analyte (e.g., mAb-8A2).

A typical sandwich assay using monoclonal antibodies mAb-4E6 and mAb-8A2 is as follows. It is based on the binding of immunoreactive material to the wells of microtiter plates coated with the monoclonal antibody mAb-4E6 and the detection of bound immunoreactive material with the use of the monoclonal antibody mAb-8A2 labeled with peroxidase. This version of the ELISA is more suited for use in the clinical laboratory because it overcomes the need to prepare standard solutions of in vitro oxidized and/or aldehyde-modified LDL.

Standard preparations and plasma samples are diluted in PBS containing antioxidants and antiplatelet agents as described above in connection with the competitive ELISA, 180 µL aliquots of 80-fold diluted plasma and of standard solutions containing between 10 and 0.01 nM of MDA-modified LDL are applied to the wells of microtiter plates coated with mAb-4E6 (200 µL of a 4 µg/mL IgG solution), and incubated for 2 hours at room temperature. After washing, the wells are incubated for 1 hour with horseradish peroxidase conjugated mAb-8A2, IgG (final IgG concentration 65 ng/mL), and washed again. The peroxidase reaction is performed as described above in connection with the competitive ELISA. The absorbance measured at 492 nm will correlate with the log-value of the MDA-modified LDL concentration in the range between 1.5 nM and 0.3 nM.

Tests for the third marker (e.g., CK-MB, troponin I) are known. See, e.g., Adams et al., *Circulation* 1993, 88(1): 101-106; Antman et al., *N. Eng. J. Med.* 1996, 335(18): 1342-1349; Hamm et al., *N. Eng J. Med.* 1997, 337(23): 1648-1653; Ohman et al., *N. Eng. J. Med.* 1996, 335(18): 1333-1341; and Van de Werf, *N. Eng. J. Med.* 1996, 335(18): 1388-1389.

As used herein, "a human patient from the general population" should be understood broadly to be any human being and is not limited to human beings who have been formally admitted to hospitals or who do or do not have specific diseases, conditions, or syndromes. There may possibly be one or more subgroups of the general population for which the method of this invention is not as desirable; however, what those one or more subgroups are (if they exist at all) is not known at present.

The "sample from the patient" used herein may be any sample that allows the benefits of this invention to be achieved. Typically, the "sample from the patient" will be a fluid sample, typically whole blood or a fluid derived from whole blood (such as plasma or serum). Fluid samples (particularly whole blood, plasma, or serum), as opposed to tissue samples, have the advantage of being easily and quickly obtained and tested, which is particularly important in a clinical setting where time may be of the essence. Also, clinicians are accustomed to withdrawing fluid samples (particularly blood) from patients, and some of the markers may not be present or may not be present in sufficient quantities in tissue samples.

Whole blood may contain substances, e.g., cells, that interfere with the tests used in the method of the invention and, therefore, whole blood is a less preferred sample. The preferred sample is plasma, which is whole blood from which the cells (red blood cells, white blood cells, and platelets) have been removed, e.g., by centrifugation. Serum is plasma from which the fibrinogen has been removed (e.g., by causing clotting and then removing the clotted material) and is also less preferred than plasma.

As indicated above, any assays, methodology, and equipment may be used provided the benefits of this invention can be achieved. Thus, for example, the invention is not limited to the use of microwell plate technology. If, for example, the tests of the method of this invention involve using antibodies, those antibodies may be used in a wide variety of automated immunologic assay systems, which include chemiluminescent immunoassay systems, microparticle enzyme immunoassay systems, fluorescence polarization immunoassay systems, and radioimmunoassay systems.

The method of this invention was used in connection with almost three hundred patients from the general population (who in this case did not include heart transplant individuals), as described below. Broadly speaking, statistical analyses of the results indicated that of the possible markers tested, the best marker for the first test was OxLDL, that the best marker for the second test was MDA-modified LDL, and that the best marker for the third test was troponin I.

A total of 286 individuals associated with the University Hospital Of Leuven either as employees or as individuals who were brought to the emergency department and/or admitted to the Hospital were studied: 105 patients with acute coronary syndromes, 64 patients with stable CAD, and 117 controls.

Individuals were classified as having an acute coronary syndrome (i.e., having an acute stage of coronary artery disease) if they had ischemic chest discomfort with ST-segment elevation or depression of more than 0.5 mm or T wave inversion of more than 1 mm. Of the individuals having an acute stage of coronary artery disease, those whose elevated creatine kinase (CK)-MB levels (and at least 3% of total CK) were present at the time of admission or in samples taken at 6 to 8 hours after admission were classified as having AMI. Alternatively, those acute-stage individuals who had no such CK-MB elevations were classified as having unstable angina.

Individuals with angiographically documented CAD and no clinical signs of ischemia within the previous month were considered to have stable CAD (i.e., in this case, stable angina).

One hundred seventeen individuals (72 males/45 females; mean age=55 years) without a history of atherosclerotic cardiovascular disease were used as controls. They were selected from laboratory and clinical staff of the Hospital and from a population of individuals admitted to the Hospital who did not have a history of atherosclerotic cardiovascular disease.

Venous blood samples were taken in the fasting state in controls and in individuals with stable angina. In individuals with acute coronary syndromes, blood samples were taken on admission before the start of treatment. Blood samples were collected on 0.01 M citrate, containing 1 mM EDTA, 20 µM vitamin E, 10 µM butylated hydroxytoluene, 20 µM dipyridamole, and 15 mM theophylline to prevent in vitro LDL oxidation and platelet activation. Blood samples were centrifuged at 3,000 g for 15 minutes at room temperature within 1 hour of collection and the resulting plasma was stored at −20° C. until the assays were performed.

LDL were isolated from pooled plasma of fasting normolipidemic donors by density gradient ultracentrifugation (Havel et al., *J. Clin. Invest.* 1955, 34: 1345-1353). MDA-modified LDL and copper-oxidized LDL were prepared as described in Haberland et al., *Proc. Natl. Acad Sci USA.* 1982, 79: 1712-1716, and Steinbrecher, *J. Biol. Chem.* 1987, 262 (8): 3603-3608, and were used as standards. Characterization of modified LDL involved measurement of thiobarbituric acid reactive substances ("TBARS"), determination of electrophoretic mobility on 1% agarose gels, quantitation of cholesterol and fatty acids by HPLC on a Nova-Pak C-18 reversed-phase column (Waters Associates, Milford, Mass.), quantitation of proteins by Lowry assay, and of phospholipids by enzymatic assay (Biomérieux, Marcy, France). See Holvoet, Collen, et al., *Arterioscler. Thromb. Vasc. Biol.* 1998, 18(1): 100-107, and Holvoet, Collen, et al. *J. Clin. Invest.* 1995, 95: 2611-2619. Apo B-100 molecules of in vitro MDA-modified LDL and of copper-oxidized LDL contained on average 244 and 210 substituted lysines, respectively. As noted above, although the extent of lysine substitution of in vitro MDA-modified LDL and copper-oxidized LDL is very similar, the lipid moiety in MDA-modified LDL is not oxidized.

A mAb-4E6 based ELISA was used for the quantitation of OxLDL in plasma (see Holvoet, Collen, et al., *Arterioscler. Thromb. Vasc. Biol.* 1998, 18(1): 100-107; Holvoet, Collen, et al., *Thromb. Haemost.* 1996, 76(5): 663-669; Holvoet and Collen, *Arterioscler. Thromb. Vasc. Biol.* 1997, 17(11): 2376-2382; and Holvoet, Collen, et al., *Arterioscler. Thromb. Vasc. Biol.* 1998, 18: 415-422). This monoclonal antibody allows the detection of 0.025 mg/dL MDA-modified LDL or copper-oxidized LDL in the presence of 500 mg/dL native LDL. Plasma levels of MDA-modified LDL were measured in a mAb-1H11 based ELISA (see Holvoet, Collen, et al., *J. Clin. Invest.* 1995, 95: 2611-2619). This monoclonal antibody allows the detection of 0.025 mg/dL MDA-modified LDL, but not of copper-oxidized LDL, in the presence of 500 mg/dL native LDL. Because the specificities of the two antibodies depend on the extent of protein modification, all lipoprotein concentrations are expressed in terms of protein.

Total cholesterol, HDL cholesterol, and triglycerides were measured by enzymatic methods (Boehringer Mannheim, Meylon, France). LDL cholesterol values were calculated with the Friedewald formula. Troponin I levels were measured on a Beckman ACCESS immunoanalyzer using commercially available monoclonal antibodies (Sanofi, Toulouse, France). C-reactive protein levels were measured in a commercial immunoassay (Boehringer, Brussels, Belgium), and plasma levels of D-dimer were measured in an ELISA as described previously (see Declerck, Holvoet, Collen, et al., *Thromb. Haemost.* 1987, 58(4): 1024-1029). C-reactive protein is a marker of inflammation. D-dimer is a marker for thrombotic syndromes.

The values obtained are shown in Table III, below ("n" indicates the number of individuals independently known to be in each category).

unstable angina pectoris, and 3.5-fold higher (p<0.001) in the 63 patients with AMI. (For comparison, a group of 79 heart transplant patients without CAD had OxLDL of 1.27±0.061 mg/dL or 1.5-fold higher than the 117 controls and a group of 28 heart transplant patients with stable CAD had OxLDL of 2.49±0.18 mg/dL or 2.9-fold higher than the controls. The reason for the apparent difference between the values for the non-CAD individuals who have had or have not had heart transplants is not known with certainty.) These results show that the test or assay of this invention used for detecting a marker of coronary artery disease in a patient in the general population will distinguish with a very high degree of diagnostic accuracy between the following categories 1 and 2: (1) those who do not have coronary artery disease and (2) those who do have one of the categories or stages of coronary artery disease, but by itself is not able to distinguish with a sufficient degree of accuracy between the categories (or stages) of coronary artery disease.

Plasma levels of MDA-modified LDL were 0.39±0.15 mg/dL in the 117 controls, were only 1.2-fold higher in the 64 patients with stable angina pectoris, but were 2.7-fold higher (p<0.001) in the 42 patients with unstable angina pectoris and 3.1-fold higher (p<0.001) in the 63 AMI patients. (For comparison, a group of 79 heart transplant patients without CAD had MDA-modified LDL of 0.38±0.016 mg/dL or essentially the same as the 117 controls and a group of 28 heart transplant patients with stable CAD had MDA-modified LDL of 0.39±0.038 mg/dL or also essentially the same as the controls.) These results show that the test or assay of this invention for detecting a marker of an acute stage of coronary artery disease will distinguish between the following categories 1 and 2: (1) those who do not have an acute stage of coronary artery disease (i.e., those who have either (a) no coronary artery disease or have non-acute coronary artery disease, namely, (b) asymptomatic coronary artery disease or (c) stable angina) but by itself will generally not be able to distinguish with a sufficient degree of accuracy between those three categories a, b, and c, and (2) those who do have one of the two categories or stages of acute coronary artery disease (i.e., those who have either (a) unstable angina or (b) acute myocardial infarction) but by itself will generally not be able to distinguish with a sufficient degree of accuracy between the two acute categories.

TABLE III

|  | Controls (n = 117) | Stable angina (n = 64) | Unstable angina (n = 42) | AMI (n = 63) |
| --- | --- | --- | --- | --- |
| Age | 55 ± 11 | 65 ± 10 | 72 ± 12 | 63 ± 11 |
| Male/female ratio | 72/45 | 53/11 | 28/14 | 42/21 |
| Total cholesterol (mg/dL) | 180 ± 31 | 180 ± 35.3 | 175 ± 36.9 | 175 ± 37.2 |
| LDL cholesterol (mg/dL) | 110 ± 26 | 115 ± 30 | 109 ± 33.4 | 111 ± 32.4 |
| HDL cholesterol (mg/dL) | 49 ± 18 | 37.6 ± 13.2 | 45.2 ± 15.6 | 37.5 ± 9.7 |
| Triglycerides (mg/dL) | 137 ± 66 | 123 ± 46.2 | 103 ± 55.4 | 125 ± 56.7 |
| Oxidized LDL (mg/dL) | 0.85 ± 0.54 | 2.65 ± 0.97 | 3.22 ± 0.85 | 2.97 ± 1.02 |
| MDA-modified LDL (mg/dL) | 0.39 ± 0.15 | 0.46 ± 0.20 | 1.07 ± 0.28 | 1.19 ± 0.43 |
| Troponin I (ng/mL) | 0.0092 ± 0.011 | 0.035 ± 0.12 | 0.37 ± 0.66 | 1.30 ± 1.08 |
| C-reactive protein (mg/dL) | 3.38 ± 1.79 | 6.28 ± 9.0 | 17.4 ± 29.8 | 18.2 ± 35.5 |
| D-dimer (μg/dL) | 166 ± 162 | 299 ± 208 | 367 ± 340 | 602 ± 632 |

Quantitative data represent means ± standard deviations.
"AMI" is acute myocardial infarction.

Plasma levels of OxLDL were 0.85±0.54 mg/dL (mean±standard deviation) in the 117 controls, and were 3.1-fold higher (p<0.001) in the 64 patients with stable angina pectoris, 3.8-fold higher (p<0.001) in the 42 patients with Plasma levels of troponin I were 0.0092±0.011 ng/mL in the 117 controls, were only 3.8-fold higher in the 64 patients with stable angina, but were 40-fold higher (p<0.001) in the 42 patients with unstable angina and 141-fold higher (p<0.001) in the 63 AMI patients. In agreement with previously published data, troponin I was found to be a marker of acute myocardial infarction (see Adams et al., *Circulation*, 1993, 88(1): 101-106; and Antman et al., *N. Eng. J. Med.* 1996, 335(18): 1342-1349).

Plasma levels of C-reactive protein were 3.38±1.79 mg/dL in the 117 controls, were only 1.9-fold higher in the 64 patients with stable angina, but were 5.1-fold higher (p<0.001) in the 42 patients with unstable angina and 5.4-fold higher in the 63 AMI patients (p<0.001). In agreement with previously published data, C-reactive protein was found to be a marker of acute coronary syndromes (see Muldoon et al., Ryan et al., Oltrona et al., and Liuzzo et al., letters and reply by authors, *N. Engl. J. Med.* 1995, 332(6): 398-400).

Plasma levels of D-dimer were 166±162 μg/dL in the 117 controls, were only 1.8-fold higher in the 64 patients with stable angina, but were 2.2-fold higher (p<0.001) in the 42 patients with unstable angina and 3.6-fold higher in the 63 AMI patients (p<0.001). In agreement with earlier published data, D-dimer was found to be a marker of acute coronary syndromes (Hoffmeister, *Circulation* 1995, 91(10): 2520-2527).

The data were also analyzed to determine the sensitivity and specificity of OxLDL (cut-point of 1.4 mg/dL), MDA-modified LDL (cut-point of 0.7 mg/dL), and troponin I (cut-point of 0.07 ng/mL) for the individual stages of coronary artery disease. In other words, below the cut-point, the individual is classified as not having the stage of CAD in question, and at or above the cut-point, the individual is classified as having that stage of CAD. The sensitivities and specificities are shown in Table IV as follows.

TABLE IV

For Acute Myocardial Infarction:

| | | |
|---|---|---|
| OxLDL | Sensitivity = 97% | Specificity = 100% |
| MDA-modified LDL | Sensitivity = 94% | Specificity = 94% |
| Troponin I | Sensitivity = 90% | Specificity = 94% |

For Unstable Angina:

| | | |
|---|---|---|
| OxLDL | Sensitivity = 100% | Specificity = 100% |
| MDA-modified LDL | Sensitivity = 95% | Specificity = 94% |
| Troponin I | Sensitivity = 33% | Specificity = 94% |

For Stable Angina:

| | | |
|---|---|---|
| OxLDL | Sensitivity = 94% | Specificity = 100% |
| MDA-modified LDL | Sensitivity = 7.8% | Specificity = 97% |
| Troponin I | Sensitivity = 6.3% | Specificity = 100% |

The data were compared using nonparametric Kruskal-Wallis ANOVA followed by Dunnet's multiple comparison test using the Prism statistical program (Graph Pad Software, San Diego, Calif.). Plasma levels of OxLDL and of MDA-modified LDL in patients with normal or elevated levels of troponin I, C-reactive protein, or D-dimer, and in patients with and without peripheral vascular disease were compared by Mann-Whitney test. Discontinuous parameters were compared by Chi-square analysis.

A logistic regression model was used to describe univariately the relation between CAD (yes or no, i.e., does the individual have CAD or not) and several covariates. For the individuals who had CAD, the relation between the stability of the CAD (stable or unstable) and the covariates was checked by logistic regression models. For the individuals who had an unstable CAD, the relation between unstable angina or AMI and the covariates was checked by logistic regression models. The relations between (1) stable or unstable angina, (2) stable angina or AMI, and (3) stable angina, unstable angina, or AMI and the covariates were examined by (multigroup for the latter) logistic regression models. For continuous variables, cubic spline functions were used to model the relationship between the covariates and the response. This allowed specifying non-linear functions of the predictors in the model. A multiple logistic regression model was fitted, including all univariately significant variables and their confounding factors. The confounding factors were checked by means of a Spearman correlation coefficient. The measure of predictive discrimination used to characterize the model performance was the area under the Receiver Operating Characteristic (ROC) curve. The software used was FE Harell Jr., "Design, S Functions For Biostatistical/Epidemiologic Modeling, Testing, Estimation, Validation, Graphics, And Prediction" (available from statlib.cmu.edu; request "send design from S," 1994); S-plus® 4.0 Release 3 for Windows (Mathsoft Inc., Cambridge, Mass., USA); and SAS/STAT software version 6.12: SAS Institute Inc. (Cary, N.C., USA).

Table V, below, shows the results of the simple logistic regression analyses for describing the ability of each of the parameters to distinguish individuals without coronary artery disease from those with coronary artery disease.

TABLE V

| | Parameter | | | |
|---|---|---|---|---|
| | $\chi^2$ | df | p-value | Area under the ROC-curve (AUC) |
| Total cholesterol | 115.06 | 4 | 0.0046 | 0.623 |
| LDL | 9.93 | 4 | 0.0416 | 0.591 |
| HDL | 26.49 | 2 | <0.0001 | 0.671 |
| Total chol/HDL chol. Ratio | 14.48 | 1 | 0.0001 | 0.630 |
| Triglycerides | 4.20 | 2 | 0.1227 | 0.576 |
| Oxidized LDL | 47.80 | 2 | <0.0001 | 0.992 |
| MDA-LDL | 24.11 | 2 | <0.0001 | 0.826 |

The area under the ROC-curve ("AUC") is 0.992 for OxLDL, which is almost a perfect score (1 is the maximum AUC). This indicates that the clinical presence of OxLDL above a predetermined level can indicate with a very high degree of diagnostic accuracy the presence of coronary artery disease as opposed to the absence of CAD. In fact, the very high degree of diagnostic accuracy is above the most preferred AUC minimum of 0.98. The only other AUC value that is anywhere near that value for OxLDL is the AUC value for MDA-modified LDL, which is 0.826, but even that is below the minimum of 0.875 for a "very high degree of diagnostic accuracy." All the other AUC values are substantially lower. For example, for total cholesterol, which for the last decade or so has been the classic marker for determining whether someone has or is at risk for CAD, is only 0.623, which is a "rather low accuracy" (see Zweig et al., "ROC Curve Analysis: An Example Showing The Relationships Among Serum Lipid And Apolipoprotein Concentrations In Identifying Patients With Coronary Artery Disease," *Clin. Chem.* 1992, 38(8): 1425-1428, citing Swets, "Measuring The Accuracy Of Diagnostic Systems," *Science* 1988, 240: 1285-1293).

Table VI, below, shows the results of the simple logistic regression analyses for describing the ability of each of the parameters to distinguish between an acute stage of coronary artery disease (i.e., either unstable angina or acute myocardial infarction) and a non-acute stage.

TABLE VI

| | Parameter | | | |
|---|---|---|---|---|
| | $\chi^2$ | df | p-value | Area under the ROC-curve (AUC) |
| Total cholesterol | 0.00 | 1 | 0.9464 | 0.520 |
| LDL | 0.12 | 1 | 0.7278 | 0.503 |
| HDL | 4.8 | 1 | 0.0285 | 0.570 |
| Total chol/HDL chol. Ratio | 1.79 | 1 | 0.1815 | 0.555 |
| triglycerides | 7.45 | 2 | 0.0241 | 0.618 |
| Oxidized LDL | 13.33 | 5 | 0.0098 | 0.672 |
| MDA-LDL | 18.66 | 3 | 0.0003 | 0.967 |
| Troponin | 24.42 | 2 | <0.0001 | 0.848 |
| C-reactive protein | 19.93 | 2 | <0.0001 | 0.710 |
| D-dimer | 5.32 | 1 | 0.0211 | 0.595 |

The area under the ROC-curve ("AUC") is 0.967 for MDA-modified LDL, which is a very high score. This indicates that the clinical presence of MDA-modified LDL above a predetermined level can indicate with a very high degree of diagnostic accuracy the presence of an acute stage of coronary artery disease (as opposed to a non-acute stage). In fact, the very high degree of diagnostic accuracy is above the preferred AUC minimum of 0.95. The only other AUC value that is anywhere near that value for MDA-modified LDL is the AUC value for troponin I, which is 0.848. All the other AUC values are substantially lower.

Table VII, below, shows the results of the simple logistic regression analyses for describing the ability of each of the parameters to distinguish between unstable angina and acute myocardial infarction.

TABLE VII

| | Parameter | | | |
|---|---|---|---|---|
| | $\chi^2$ | d.f. | p-value | Area under the ROC-curve (AUC) |
| Total cholesterol | 2.00 | 1 | 0.1572 | 0.598 |
| LDL | 0.11 | 1 | 0.7451 | 0.531 |
| HDL | 5.75 | 1 | 0.0165 | 0.625 |
| Total chol/HDL chol. Ratio | 0.6 | 1 | 0.4371 | 0.587 |
| triglycerides | 1.64 | 1 | 0.1997 | 0.539 |
| Oxidized LDL | 1.62 | 1 | 0.2028 | 0.579 |
| MDA-LDL | 1.66 | 1 | 0.1977 | 0.586 |
| Troponin | 22.26 | 2 | <0.0001 | 0.777 |
| C-reactive protein | 5.24 | 2 | 0.0730 | 0.637 |
| D-dimer | 0.16 | 1 | 0.6892 | 0.568 |

The area under the ROC-curve ("AUC") is 0.777 for troponin I, which, according to Swets (quoted in Zweig et al., *Clin. Chem.* 1992, 38(8): 1425-1428, above), indicates an accuracy useful for some purposes. This AUC value of 0.777 indicates that the clinical presence of troponin I above a predetermined level can indicate with a high degree of diagnostic accuracy the presence of acute myocardial infarction (as opposed to unstable angina). In fact, the high degree of diagnostic accuracy is well above the preferred AUC minimum of 0.70. The next highest AUC value is the AUC value for C-reactive protein, which is 0.637. All the other AUC values, including those for OxLDL and MDA-modified LDL are substantially lower and are barely above the minimum AUC value of 0.5.

Table VIII, below, shows the results of the simple logistic regression analyses for describing the relation between each of the parameters and distinguishing between stable coronary artery disease (either asymptomatic coronary artery disease or stable angina) and unstable angina.

TABLE VIII

| | Parameter | | | |
|---|---|---|---|---|
| | $\chi^2$ | d.f. | p-value | Area under the ROC-curve (AUC) |
| Total cholesterol | 0.80 | 1 | 0.3709 | 0.534 |
| LDL | 0.26 | 1 | 0.6122 | 0.526 |
| HDL | 0.28 | 1 | 0.5998 | 0.507 |
| Total chol/HDL chol. Ratio | 0.34 | 1 | 0.5618 | 0.514 |
| triglycerides | 10.08 | 4 | 0.0391 | 0.701 |
| Oxidized LDL | 10.53 | 3 | 0.0415 | 0.689 |
| MDA-LDL | 24.56 | 1 | <0.0001 | 0.997 |
| Troponin | 14.88 | 2 | 0.0006 | 0.743 |
| C-reactive protein | 9.05 | 2 | 0.0108 | 0.631 |
| D-dimer | 4.66 | 1 | 0.0308 | 0.641 |

The AUC for MDA-modified LDL is 0.997 (almost a perfect value of 1), which shows that using MDA-modified LDL as marker can distinguish with a very high degree of diagnostic accuracy between stable coronary artery disease and unstable angina. No other parameter comes close to matching the accuracy of MDA-modified LDL.

Table IX, below, shows the results of the simple logistic regression analyses for describing the relation between each of the parameters and distinguishing between stable coronary artery disease (either asymptomatic coronary artery disease or stable angina) and acute myocardial infarction.

TABLE IX

| | Parameter | | | |
|---|---|---|---|---|
| | $\chi^2$ | d.f. | p-value | Area under the ROC-curve (AUC) |
| Total cholesterol | 0.58 | 1 | 0.4448 | 0.573 |
| LDL | 0.03 | 1 | 0.8742 | 0.488 |
| HDL | 7.27 | 1 | 0.0070 | 0.613 |
| Total chol/HDL chol. Ratio | 2.56 | 1 | 0.1098 | 0.585 |
| triglycerides | 5.49 | 2 | 0.0644 | 0.617 |
| Oxidized LDL | 4.21 | 1 | 0.0401 | 0.585 |
| MDA-LDL | 23.74 | 2 | <0.0001 | 0.967 |
| Troponin | 28.75 | 2 | <0.0001 | 0.921 |
| C-reactive protein | 25.60 | 2 | <0.0001 | 0.763 |
| D-dimer | 4.19 | 1 | 0.0406 | 0.562 |

The AUC for MDA-modified LDL is 0.967, which shows that using MDA-modified LDL as marker can distinguish with a very high degree of diagnostic accuracy between stable coronary artery disease and acute myocardial infarction. Troponin I, with an AUC value of 0.921 is good but not nearly as perfect. The next highest AUC value is 0.763, for C-reactive protein, but that is significantly lower than the MDA-modified LDL and troponin I AUC values.

All of these results show that the present invention provides a method having a clinically sufficient degree of diagnostic accuracy for detecting the presence of and for distinguishing between or among the non-acute and the acute stages of coronary artery disease for a human patient from the general population, the non-acute stage of coronary artery disease being either asymptomatic coronary artery disease or stable angina and the acute stages of coronary artery disease being unstable angina and acute myocardial infarction.

Variations and modifications will be apparent to those skilled in the art, and the claims are intended to cover all variations and modifications that fall within the true spirit and scope of the invention.

For example, the cut-points for the various markers will depend on which markers are used and which tests are used. When using the methods described herein, the cut-point may be 1.4 mg/dL (milligrams/deciliter) for OxLDL, 0.7 mg/dL for MDA-modified LDL, and 0.07 ng/mL (nanograms/milliliter) for troponin I. However, if, for example, a non-ionic detergent such as Tween 20 (polyoxyethylenesorbitan monolaurate; Sigma Chemical Company) is included in the buffer solution (the PBS solution) with which the LDL-containing material (e.g., plasma, standard, or control) is incubated (e.g., in a concentration in the buffer solution of up to about 1% w/v [weight/volume], with a value in the range of about 0.2% w/v to about 0.6% w/v appearing to be optimum), the OxLDL and MDA-modified LDL values may be significantly increased, in which case the respective cut-points would have to be increased. Without wishing to be bound by any theory, it is believed that a non-ionic detergent will separate the protein portion from the lipid portion of the OxLDL and MDA-modified LDL, that the preferred monoclonal antibodies mAb-4E6 and mAb-1H11 are directed to epitopes on the protein portion, and that removing the lipid portion from the protein portion removes steric hindrance and allows the antibody to bind to more sites on the same protein portion, thereby increasing the total amount of antibody that binds to a given amount of OxLDL or MDA-modified LDL. Thus, it has been observed that use of Tween 20 in a concentration of 0.2% w/v to 0.6% w/v in the buffer with a freshly drawn plasma sample increased the reported amount of OxLDL in the sample by a factor of over 10-fold as compared to when no Tween 20 was used in the buffer for the same sample amount of the same plasma. That is desirable because, broadly speaking, having a larger range for a marker whose presence above a predetermined value in a test indicates the presence of a disease, condition, or syndrome can increase the accuracy of the test.

We claim:

1. A method for diagnosing coronary artery disease comprising performing steps (a), (c), and (e) and at least one of steps (b) and (d):
   (a) obtaining one or more human samples comprising whole blood or a fluid derived from whole blood;
   (b) comparing a level of oxidized low density lipoprotein (OxLDL) having at least 60 aldehyde-modified lysine residues per apolipoprotein B-100 (apo B-100) moiety in one of the one or more human samples to the level of the OxLDL in a control;
   (c) comparing a level of malondialdehyde-modified low density lipoprotein (MDA-modified LDL) having at least 60 aldehyde-modified lysine residues per apolipoprotein B-100 (apo B-100) moiety in one of the one or more human samples to the level of the MDA-modified LDL in a control;
   (d) comparing a level of a heart protein that is a marker for acute myocardial infarction in one of the one or more human samples to the level of the heart protein in a control; and
   (e) making a diagnosis based on results from step (c) and at least one of steps (b) and (d) from the following matrix if steps (b), (c), and (d) are all performed:

| 1.1 Indication | (b) | (c) | (d) |
|---|---|---|---|
| the individual does not have coronary artery disease | − | − | − |
| the individual has chronic coronary artery disease | + | − | − |
| the individual has unstable angina | + | + | − |
| the individual has acute myocardial infarction of atherosclerotic origin | + | + | + |
| the individual has acute myocardial infarction of non-atherosclerotic origin | − | − | + | or making a diagnosis based on results from step (c) and at least one of steps (b) and (d) from the following matrix if steps (b) and (c) are performed:

| 1.2 Indication | (b) | (c) |
|---|---|---|
| the individual does not have coronary artery disease | − | − |
| the individual has chronic coronary artery disease | + | − |
| the individual has acute coronary artery disease | + | + | or making a diagnosis based on results from step (c) and at least one of steps (b) and (d) from the following matrix if steps (C) and (d) are performed:

| 1.3 Indication | (c) | (d) |
|---|---|---|
| the individual does not have acute coronary artery disease | − | − |
| the individual has unstable angina | + | − |
| the individual has acute myocardial infarction of non-atherosclerotic origin | − | + |
| the individual has acute myocardial infarction of atherosclerotic origin | + | + | wherein "+" indicates that the level of the OxLDL, MDA-modified LDL, and heart protein in the human sample is higher compared to the level of the OxLDL, MDA-modified LDL, and heart protein in the control and "−" indicates that the level of the OxLDL, MDA-modified LDL, and heart protein in the human sample is not higher compared to the level of the OxLDL, MDA-modified LDL, and heart protein in the control, the control providing results based on those of a normal control population.

2. The method of claim 1 wherein at least one of steps (b), (c), and (d) is performed based on the result of an immunological assay.

3. The method of claim 2 wherein the immunological assay is a competitive assay or a sandwich assay.

4. The method of claim 2 wherein at least one assay utilizes a monoclonal antibody selected from the group consisting of mAb-4E6, mAb-1H11, mAb-8A2, a monoclonal antibody having a high affinity for a CK-MB or a troponin, and combinations thereof; the monoclonal antibodies mAb-4E6, mAb-1H11, and mAb-8A2 being produced, respectively, by hybridomas Hyb4E6, Hyb1H11, and Hyb8A2, which were deposited on Apr. 24, 1997 at the Belgian Coordinated Collections Of Microorganisms under accession numbers, respectively, of LMBP 1660 CB, LMBP 1659 CB, and LMBP 1661 CB.

5. The method of claim 1 wherein steps (a), (b), (c), and (e) are performed.

6. The method of claim 1 wherein steps (a), (c), (d), and (e) are performed.

7. The method of claim 1 wherein steps (a), (b), (c), (d), and (e) are performed.

8. The method of claim 1 wherein at least one human sample is plasma.

9. The method of claim 1 wherein at least one human sample is serum.

10. The method of claim 1 wherein the level in the control for each of OxLDL, MDA-modified LDL, and heart protein is representative of the level in a sampling of individuals of a general population who have no history of atherosclerotic cardiovascular disease.

11. A method for diagnosing coronary artery disease comprising performing steps (a), (c), and (e) and at least one of steps (b) and (d):
   (a) obtaining one or more human samples comprising whole blood or a fluid derived from whole blood;
   (b) performing an immunological assay using mAb-4E6 on one of the one or more human samples and comparing a level of oxidized LDL (OxLDL) having at least 60 aldehyde-modified lysine residues per apolipoprotein B-100 (apo B-100) moiety in the human sample from the assay to the level of the OxLDL in a control; the monoclonal antibody mAb-4E6 being produced by hybridoma Hyb4E6, which was deposited on Apr. 24, 1997 at the Belgian Coordinated Collections Of Microorganisms under accession number LMBP 1660 CB;
   (c) performing an immunological assay using mAb-1H11 on one of the one or more human samples and comparing a level of malondialdehyde-modified low density lipoprotein (MDA-modified LDL) having at least 60 aldehyde-modified lysine residues per apolipoprotein B-100 (apo B-100) moiety in the human sample from the assay to the level of the MDA-modified LDL in a control; the monoclonal antibody mAb-1H11 being produced by hybridoma Hyb1H11, which was deposited on Apr. 24, 1997 at the Belgian Coordinated Collections Of Microorganisms under accession number LMBP 1659 CB
   (d) performing an assay for a heart protein that is a marker for acute myocardial infarction on one of the one or more human samples and comparing a level of a heart protein in the human sample from the assay to the level of the heart protein in a control; and
   (e) making a diagnosis based on results from step (c) and at least one of steps (b) and (d) from the following matrix if steps (b), (c), and (d) are all performed:

| 1.4 Indication | (b) | (c) | (d) |
| --- | --- | --- | --- |
| the individual does not have coronary artery disease | – | – | – |
| the individual has chronic coronary artery disease | + | – | – |
| the individual has unstable angina | + | + | – |
| the individual has acute myocardial infarction of atherosclerotic origin | + | + | + |
| the individual has acute myocardial infarction of non-atherosclerotic origin | – | – | + | or making a diagnosis based on results from step (c) and at least one of steps (b) and (d) from the following matrix if steps (b) and (c) are performed:

| 1.5 Indication | (b) | (c) |
| --- | --- | --- |
| the individual does not have coronary artery disease | – | – |
| the individual has chronic coronary artery disease | + | – |
| the individual has acute coronary artery disease | + | + | or making a diagnosis based on results from step (c) and at least one of steps (b) and (d) from the following matrix if steps (c) and (d) are performed:

| 1.6 Indication | (c) | (d) |
| --- | --- | --- |
| the individual does not have acute coronary artery disease | – | – |
| the individual has unstable angina | + | – |
| the individual has acute myocardial infarction of non-atherosclerotic origin | – | + |
| the individual has acute myocardial infarction of atherosclerotic origin | + | + | wherein "+" indicates that the level of the OxLDL, MDA-modified LDL, and heart protein in the human sample is higher compared to the level of the OxLDL, MDA-modified LDL, and heart protein in the control and "–" indicates that the level of the OxLDL, MDA-modified LDL, and heart protein in the human sample is not higher compared to the level of the OxLDL, MDA-modified LDL, and heart protein in the control, the control providing results based on those of a normal control population.

12. The method of claim 11 wherein steps (a), (b), (c), and (e) are performed.

13. The method of claim 11 wherein steps (a), (c), (d), and (e) are performed.

14. The method of claim 11 wherein steps (a), (b), (c), (d), and (e) are performed.

15. The method of claim 11 wherein at least one human sample is plasma.

16. The method of claim 11 wherein at least one human sample is serum.

17. The method of claim 11 wherein the level in the control for each of OxLDL, MDA-modified LDL, and heart protein is representative of the level in a sampling of individuals of a general population who have no history of atherosclerotic cardiovascular disease.

* * * * *